United States Patent
Schaeffer et al.

(10) Patent No.: US 10,349,958 B2
(45) Date of Patent: Jul. 16, 2019

(54) LITHOTRIPSY PROBES AND METHODS FOR PERFORMING LITHOTRIPSY

(71) Applicant: Cook Medical Technologies LLC, Bloomington, IN (US)

(72) Inventors: Darin Schaeffer, Bloomington, IN (US); Pamela Ridgley, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 1558 days.

(21) Appl. No.: 13/833,323

(22) Filed: Mar. 15, 2013

(65) Prior Publication Data
US 2013/0261639 A1 Oct. 3, 2013

Related U.S. Application Data

(60) Provisional application No. 61/616,255, filed on Mar. 27, 2012.

(51) Int. Cl.
*A61B 17/22* (2006.01)
*A61B 17/00* (2006.01)
*A61B 90/00* (2016.01)

(52) U.S. Cl.
CPC ......... *A61B 17/22012* (2013.01); *A61B 2017/00469* (2013.01); *A61B 2017/00477* (2013.01); *A61B 2017/22018* (2013.01); *A61B 2090/034* (2016.02)

(58) Field of Classification Search
CPC ........... A61B 17/22012; A61B 2017/00469
USPC ........................................................ 606/128
See application file for complete search history.

(56) References Cited

U.S. PATENT DOCUMENTS

| | | |
|---|---|---|
| 4,589,415 A | 5/1986 | Haaga |
| 4,721,107 A | 1/1988 | Bolg et al. |
| 4,726,369 A | 2/1988 | Mar |
| 4,774,947 A | 10/1988 | Falk et al. |
| 4,823,793 A | 4/1989 | Angulo et al. |
| 4,858,810 A | 8/1989 | Intlekofer et al. |
| 4,960,108 A | 10/1990 | Reichel et al. |
| 5,045,061 A | 9/1991 | Seifert et al. |

(Continued)

FOREIGN PATENT DOCUMENTS

| | | |
|---|---|---|
| EP | 1528893 | 7/2009 |
| EP | 2359776 | 8/2011 |

(Continued)

OTHER PUBLICATIONS

William Cook Europe, "Flipper Detachable Embolization Coil," 2008, pp. 1-12, Denmark.

(Continued)

*Primary Examiner* — Kathleen S Holwerda
*Assistant Examiner* — Sarah A Simpson
(74) *Attorney, Agent, or Firm* — Buchanan Van Tuinen LLC

(57) ABSTRACT

Various medical devices are described herein. More particularly, various probes used for performing lithotripsy and methods of performing lithotripsy are described. In an example, a probe comprises an elongate member comprising a proximal end, a distal end, a proximal portion, an intermediate portion, and a distal portion. The proximal portion has an outer diameter that is greater than the outer diameter of the distal portion.

9 Claims, 9 Drawing Sheets

(56) References Cited

U.S. PATENT DOCUMENTS

| | | |
|---|---|---|
| 5,065,761 A | 11/1991 | Pell |
| 5,137,288 A | 8/1992 | Starkey et al. |
| 5,159,861 A | 11/1992 | Anderson |
| 5,161,534 A | 11/1992 | Berthiaume |
| 5,163,421 A | 11/1992 | Bernstein et al. |
| 5,163,903 A | 11/1992 | Crittenden et al. |
| 5,197,968 A | 3/1993 | Clement |
| 5,199,417 A | 4/1993 | Muller et al. |
| 5,209,719 A | 5/1993 | Baruch et al. |
| 5,219,332 A | 6/1993 | Nelson et al. |
| 5,242,454 A | 9/1993 | Gundlach et al. |
| 5,273,052 A | 12/1993 | Kraus et al. |
| 5,281,230 A | 1/1994 | Heidmueller |
| 5,290,294 A | 3/1994 | Cox et al. |
| 5,312,418 A | 5/1994 | Bonnet |
| 5,325,868 A | 7/1994 | Kimmelstiel |
| 5,392,778 A | 2/1995 | Horzewski |
| 5,425,735 A | 6/1995 | Rosen et al. |
| 5,484,433 A | 1/1996 | Taylor et al. |
| 5,540,656 A | 7/1996 | Pflueger et al. |
| 5,722,980 A * | 3/1998 | Schulz ............ A61B 17/22012 604/22 |
| 5,792,145 A | 8/1998 | Bates et al. |
| 5,851,189 A | 12/1998 | Forber |
| 5,868,756 A | 2/1999 | Henry et al. |
| 5,906,623 A | 5/1999 | Peterson |
| 5,944,728 A | 8/1999 | Bates |
| 5,954,670 A | 9/1999 | Baker |
| 6,004,330 A | 12/1999 | Middleman et al. |
| 6,030,349 A | 2/2000 | Wilson et al. |
| 6,033,414 A | 3/2000 | Tockman et al. |
| 6,059,796 A | 5/2000 | Bilitz et al. |
| 6,093,748 A | 7/2000 | Ahluwalia et al. |
| 6,193,730 B1 | 2/2001 | Beland |
| 6,217,588 B1 * | 4/2001 | Jerger ............ A61B 17/22012 606/127 |
| 6,238,389 B1 | 5/2001 | Paddock et al. |
| 6,241,744 B1 | 6/2001 | Imran et al. |
| 6,264,664 B1 | 7/2001 | Avellanet |
| 6,352,534 B1 | 3/2002 | Paddock et al. |
| 6,440,123 B1 | 8/2002 | Engel |
| 6,458,137 B1 | 10/2002 | Klint |
| 6,482,203 B2 | 11/2002 | Paddock et al. |
| 6,533,772 B1 | 3/2003 | Sherts et al. |
| 6,613,014 B1 | 9/2003 | Chi |
| 6,645,223 B2 | 11/2003 | Boyle et al. |
| 6,660,013 B2 | 12/2003 | Rabiner et al. |
| 6,673,080 B2 | 1/2004 | Reynolds et al. |
| 6,695,834 B2 | 2/2004 | Gellman et al. |
| 6,866,670 B2 | 3/2005 | Rabiner et al. |
| 7,087,061 B2 | 8/2006 | Chernenko et al. |
| 7,144,378 B2 | 12/2006 | Arnott |
| 7,470,274 B2 | 12/2008 | Lebet |
| 7,682,366 B2 | 3/2010 | Sakurai et al. |
| 7,717,865 B2 | 5/2010 | Boutillette et al. |
| 7,831,297 B2 | 11/2010 | Opie et al. |
| 7,909,821 B2 | 3/2011 | Paddock et al. |
| 7,914,540 B2 | 3/2011 | Schwartz et al. |
| 7,972,282 B2 | 7/2011 | Clark et al. |
| 7,993,329 B2 | 8/2011 | Howell et al. |
| 8,038,628 B2 | 10/2011 | von Malmborg et al. |
| 8,147,481 B2 | 4/2012 | Whittaker et al. |
| 8,496,603 B2 | 7/2013 | Mamourian |
| 2001/0016712 A1 | 8/2001 | Hamilton |
| 2002/0010478 A1 * | 1/2002 | Menne ............ A61B 17/22012 606/128 |
| 2003/0069522 A1 | 4/2003 | Jacobsen et al. |
| 2003/0176873 A1 | 9/2003 | Chernenko et al. |
| 2004/0039372 A1 | 2/2004 | Carmody |
| 2004/0172116 A1 | 9/2004 | Seifert et al. |
| 2004/0215108 A1 | 10/2004 | Windheuser |
| 2005/0070820 A1 | 3/2005 | Boutillette et al. |
| 2005/0288655 A1 | 12/2005 | Root et al. |
| 2006/0229496 A1 | 10/2006 | Windheuser et al. |
| 2007/0004991 A1 | 1/2007 | Shelton |
| 2007/0010849 A1 | 1/2007 | Balgobin et al. |
| 2007/0021754 A1 | 1/2007 | Chernenko et al. |
| 2007/0179486 A1 | 8/2007 | Welch et al. |
| 2008/0132906 A1 | 6/2008 | Rasmussen |
| 2008/0147110 A1 | 6/2008 | Wijeratne |
| 2008/0312671 A1 | 12/2008 | Riles et al. |
| 2009/0118741 A1 | 5/2009 | Lebet |
| 2009/0124899 A1 | 5/2009 | Jacobs et al. |
| 2009/0124934 A1 | 5/2009 | Rabbitte et al. |
| 2010/0036294 A1 | 2/2010 | Mantell et al. |
| 2010/0100103 A1 | 4/2010 | Haskal et al. |
| 2010/0211006 A1 | 8/2010 | Schmidt-Sorensen |
| 2011/0112507 A1 | 5/2011 | Linderman et al. |
| 2012/0136425 A1 | 5/2012 | Orr |
| 2013/0018359 A1 | 1/2013 | Coyle |
| 2013/0035749 A1 | 2/2013 | Farag |
| 2013/0103001 A1 | 4/2013 | BenMaamer et al. |
| 2013/0303330 A1 | 11/2013 | Stevens et al. |

FOREIGN PATENT DOCUMENTS

| | | |
|---|---|---|
| EP | 2644134 A2 | 10/2013 |
| EP | 2644134 A3 | 10/2013 |
| WO | WO2005094936 | 10/2005 |

OTHER PUBLICATIONS

Cook Incorporated, "Retracta Detachable Embolization Coils," 2013, pp. 1-36, Bloomington, Indiana, United States.

European Patent Office, Extended European Search Report for application No. 13160954.7 dated Sep. 26, 2013, p. 1-9.

European Patent Office, Partial European Search Report, for European Application No. 13160954.7 dated Jun. 6, 2013, p. 1-5.

International Searching Authority, The International Search Report and the Written Opinion of the International Searching Authority for International Application No. PCT/US2012/054374 dated Dec. 12, 2012.

* cited by examiner

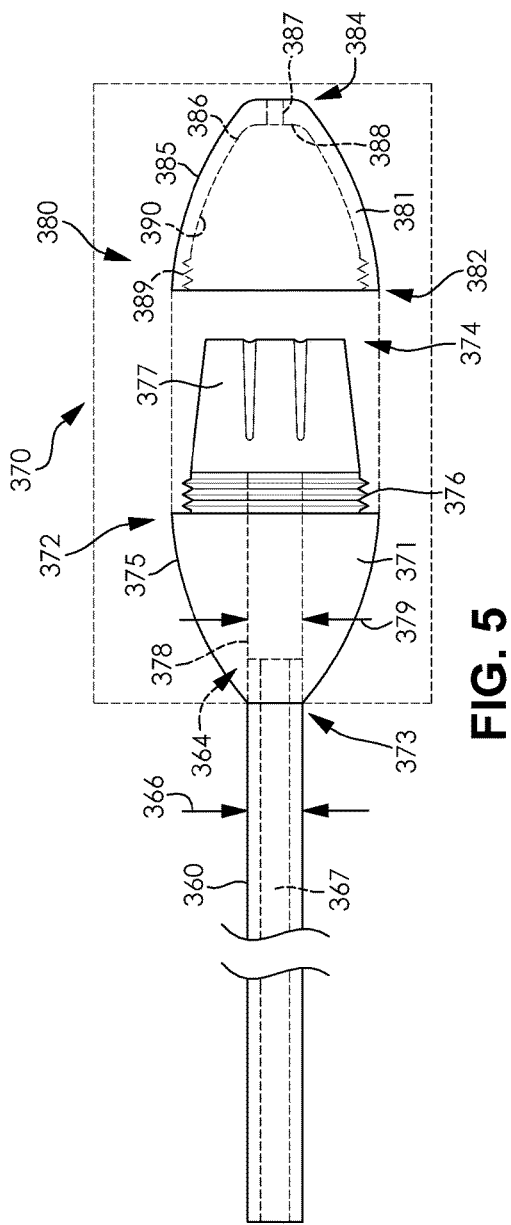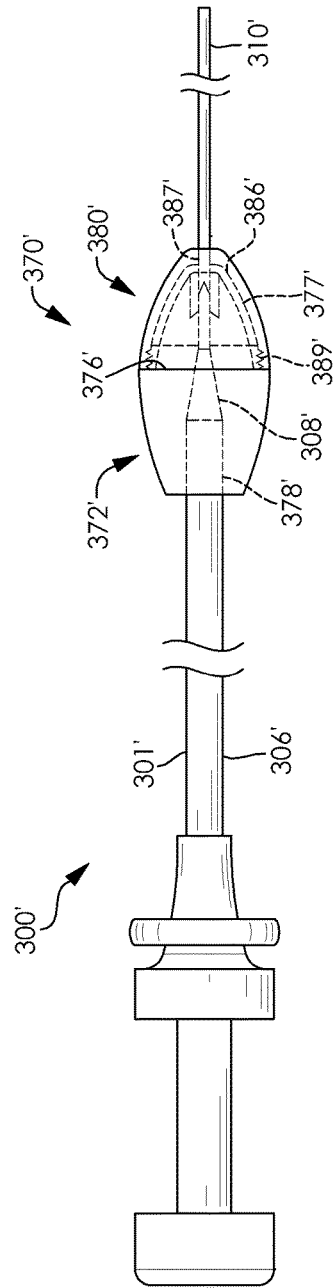
FIG. 5
FIG. 5A

LITHOTRIPSY PROBES AND METHODS FOR PERFORMING LITHOTRIPSY

RELATED APPLICATIONS

This application claims the benefit of U.S. Provisional Application No. 61/616,255, filed Mar. 27, 2012. The entire contents of this related application is hereby incorporated into this disclosure by reference.

FIELD

The disclosure relates generally to medical devices. More particularly, the disclosure relates to devices and methods for performing lithotripsy. Particular embodiments and methods useful in the removal of stones disposed in various types of bodily passages, such as salivary ducts and the urinary tract, are described.

BACKGROUND

It is sometimes necessary, or otherwise desirable, to remove unwanted materials disposed within a bodily passage. For example, lithotripsy—the disruption and removal of calculi, or stones, from a region of the body—is frequently performed to remove stones disposed in a salivary duct or the urinary tract.

Various types of lithotripsy are known, including shockwave lithotripsy, extracorporeal shockwave lithotripsy, laser lithotripsy, percutaneous lithotripsy, endoscopic lithotripsy, and pneumatic lithotripsy. In pneumatic lithotripsy, a probe attached to a firing handle is advanced through a previously placed sheath, or the working channel of a scope, until the distal end of the probe contacts a stone disposed in a bodily passage. The firing handle is activated to rapidly advance the probe to produce an impact between the distal end of the probe and the stone causing its fragmentation and enabling its removal.

Pneumatic lithotripsy can be challenging in relatively small body passages, such as the salivary ducts and urinary tract, due to the deficiencies of probes that utilize a continuous outer diameter. Such probes prevent lithotripsy from being performed in small bodily passages when the probe has a large outer diameter and increase the tendency of the probe to kink along its length when the probe has a small outer diameter. Moreover, probes having a small outside diameter reduce the capacity of the probe to transmit power along its length.

In addition, current probes fail to provide a mechanism that allows a user to have fine motor control over the probe while performing lithotripsy. With existing probes, users must rely on gross motor control to perform the procedure. For example, to adjust the length of a probe disposed in a bodily passage, a user must either manipulate the firing handle or grasp a portion of the probe itself, which is smooth and relatively small. The lack of fine motor control over the probe while performing lithotripsy decreases the efficiency of the procedure and increases the likelihood of the probe perforating the wall of the bodily passage and/or causing tissue damage, especially in relatively small bodily passages.

Scopes used to perform lithotripsy generally include optics to provide visualization of the stone that is desired to be fragmented and removed from the bodily passage. However, in some cases the stone is located within, or beyond, a curve defined by the wall of the bodily passage, or is offset from the working channel of the scope. Therefore, the scope must be manipulated (e.g., pushed into the wall of the bodily passage) such that the probe can be advanced to fragment the stone, which can result in the optics becoming obstructed by the wall of the bodily passage. This increases the complexity and time required to complete procedure because it prevents the optics from visualizing contact between the probe and the stone during treatment.

Therefore, a need exists for improved devices and methods for use in the performance of lithotripsy.

BRIEF SUMMARY

Various exemplary medical devices and methods are described and illustrated herein.

An exemplary probe for use in lithotripsy comprises an elongate member, a fitting, an elongate tubular member, and a handle. The elongate member comprises a first proximal end, a first distal end, a proximal portion, an intermediate portion, and a distal portion. The proximal portion has a first length and a first outer diameter. The intermediate portion has a second length and a second outer diameter. The distal portion has a third length and a third outer diameter. The intermediate portion is disposed between the proximal portion and the distal portion. The first outer diameter is greater than the third outer diameter and the second outer diameter of the intermediate portion tapers from the first outer diameter to the third outer diameter. The fitting is disposed on the first proximal end of the elongate member and is adapted to attach the probe to a lithotripter. The fitting comprises a second proximal end and a second distal end. The elongate tubular member is disposed over a portion of the first length of the proximal portion and comprises a third proximal end that is disposed adjacent to the second distal end of the fitting and a third distal end that is disposed proximal to the first distal end of the elongate member. The handle is disposed on the elongate member and comprises a fourth proximal end that is attached to the third distal of the elongate tubular member and a fourth distal end.

Another exemplary probe for use in lithotripsy comprises an elongate member, a fitting, an elongate tubular member, and a handle. The elongate member comprises a first proximal end, a first distal end, a proximal portion, an intermediate portion, and a distal portion. The proximal portion has a first length and a first outer diameter. The intermediate portion has a second length and a second outer diameter. The distal portion has a third length and a third outer diameter. The intermediate portion is disposed between the proximal portion and the distal portion. The first outer diameter is greater than the third outer diameter and the second outer diameter of the intermediate portion tapers from the first outer diameter to the third outer diameter. The fitting is disposed on the first proximal end of the elongate member and is adapted to attach the probe to a lithotripter. The fitting comprises a second proximal end and a second distal end. The elongate tubular member is disposed over a portion of the first length of the proximal portion and comprises a third proximal end that is disposed adjacent to the second distal end of the fitting and a third distal end that is disposed proximal to the intermediate portion. The handle is disposed over the intermediate portion of the elongate member and comprises a fourth proximal end that is attached to the third distal of the elongate tubular member and a fourth distal end.

An exemplary method of performing lithotripsy on a stone disposed in a bodily passage comprises the steps of: inserting a sheath that has a first proximal end, a first distal end, and that defines a first lumen into the bodily passage such that the first distal end is disposed in the bodily passage; inserting a scope that has a second proximal end, a second distal end, and that defines a second lumen through the first lumen such that the second distal end is disposed distal to the first distal end of the sheath; inserting a lithotripter comprising a firing handle and a probe having a third proximal end and a third distal end through the second lumen such that the third distal end is disposed distal to the second distal end of the scope; navigating the third distal end of the probe towards the stone; contacting the third distal end of the probe with the stone; and activating the firing handle of the lithotripter to fragment the stone.

Additional understanding of the exemplary medical devices and methods can be obtained by review of the detailed description, below, and the appended drawings.

BRIEF DESCRIPTION OF THE DRAWINGS

FIG. 5 is an exploded view of the elongate tubular member and handle illustrated in FIG. 3.

FIG. 5A is a side view of another exemplary probe with an associated handle.

DETAILED DESCRIPTION

The following detailed description and the appended drawings describe and illustrate various exemplary devices and methods. The description and drawings are exemplary in nature and are provided to enable one skilled in the art to make and use one or more exemplary devices and/or practice one or more exemplary methods. They are not intended to limit the scope of the claims in any manner.

The use of "e.g.," "etc.," "for instance," "in example," and "or" and grammatically related terms indicates non-exclusive alternatives without limitation, unless otherwise noted. The use of "optionally" and grammatically related terms means that the subsequently described element, event, or circumstance may or may not be present/occur, and that the description includes instances where said element, event, or circumstance occurs and instances where it does not. As used herein, the terms "proximal" and "distal" are used to describe opposing axial ends of the particular elements or features being described. The term "bodily passage" refers to any passage within the body of an animal, including, but not limited to, humans, and includes elongate passages. The term "salivary duct" refers to the parotid ducts, submandibular ducts, and/or sublingual ducts. The term "papilla" refers to the projection and opening formed at the end of a salivary duct. The term "urinary tract" refers to the kidneys, renal pelvis, ureters, bladder, urethra, and/or any other portion of the urinary system. The term "attached" refers to the fixed, releasable, or integrated association of two or more elements and/or devices. Thus, the term "attached" includes releasably attaching or fixedly attaching two or more elements. The term "exemplary" refers to "an example of" and is not intended to convey a meaning of an ideal or preferred embodiment.

Figure 1:
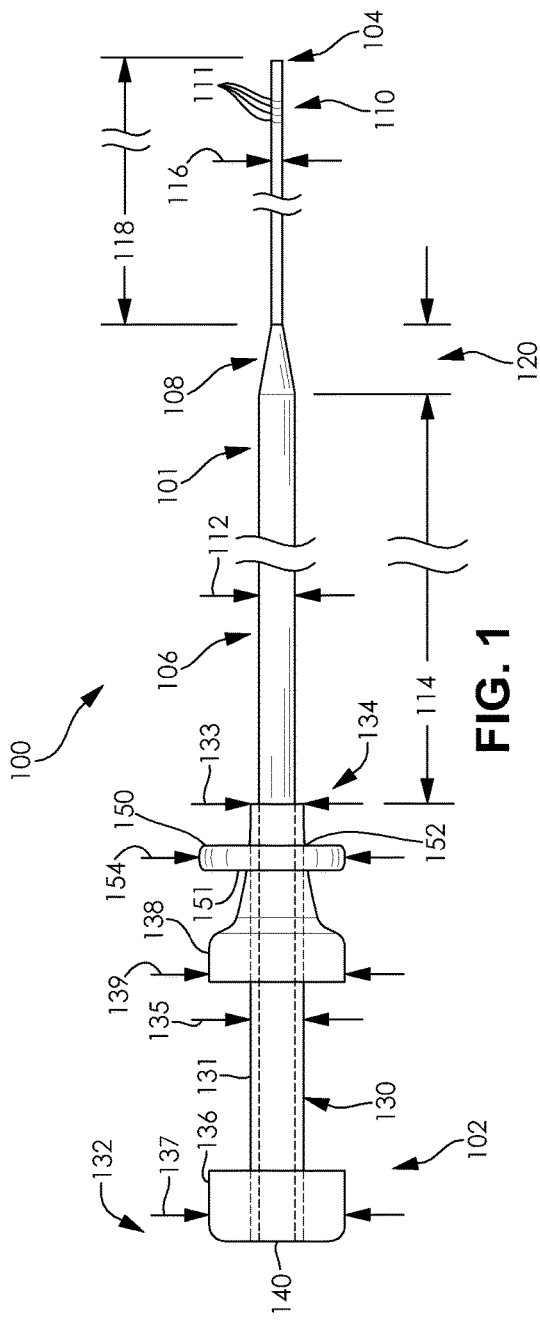
FIG. 1 is a side view of an exemplary probe.

FIG. 1 illustrates an exemplary probe 100 comprising an elongate member 101, fitting 130, and an O-ring 150.

The elongate member 101 comprises a proximal end 102, distal end 104, proximal portion 106, intermediate portion 108, and distal portion 110. Proximal portion 106 extends from the proximal end 102 to the intermediate portion 108 and has an outer diameter 112 and a length 114 that extends distal to fitting 130. Proximal portion 106 has a uniform, or substantially uniform, outer diameter 112 and is rigid, or substantially rigid, relative to the distal portion 110. Proximal portion 106 can have any suitable outer diameter 112 and length 114, and skilled artisans will be able to select a suitable outer diameter and length for the proximal portion of an elongate member according to a particular embodiment based on various considerations, such as the nature of the bodily passage, the inner diameter of the lumen of a scope or sheath within which the probe is intended to be used, the amount of energy desired to be transmitted to the distal end of the elongate member, and the desired flexibility of the elongate member. The inventor has determined that an outer diameter 112 between about 0.25 millimeters and about 2.75 millimeters is suitable. In addition, the inventor has determined that an outer diameter 112 between about 0.5 millimeters and about 2.5 millimeters is suitable. Furthermore, the inventor has determined that an outer diameter 112 about, equal to, or substantially equal to, 1.0 millimeter is considered suitable. Moreover, the inventor has determined that when the proximal portion 106 is formed of nickel titanium, an outer diameter 112 about, equal to, substantially equal to, or greater than 1.0 millimeter is considered suitable.

Intermediate portion 108 extends between proximal portion 106 and distal portion 110 and has a length 120 and an outer diameter that tapers from the proximal portion 106 to the distal portion 110. Intermediate portion 108 can have any suitable outer diameter and length 120, and a skilled artisan will be able to select a suitable outer diameter and length 120 for the intermediate portion 108 of an elongate member according to a particular embodiment based on various considerations, such as the nature of the bodily passage, the inner diameter of the lumen of a scope or sheath within which the probe is intended to be used, the amount of energy desired to be transmitted to the distal end of the elongate member, and the desired flexibility of the elongate member. An example of a length 120 considered suitable for intermediate portion 108 is a length 120 that is less than the length 114 of proximal portion 106 and the length 118 of distal portion 110. The inventor has determined that an intermediate portion 108 having a length 120 between about 2 millimeters and about 10 millimeters is suitable. Moreover, the inventor has determined that an intermediate portion 108 having a length 120 between about 5 millimeters and about 30 millimeters is suitable. In addition, the inventor has determined that an intermediate portion 108 having a length 120 about, equal to, or substantially equal to, 5 millimeters is considered suitable. Furthermore, the inventor has determined that an intermediate portion 108 having a length 120 about, equal to, or substantially equal to, 22 millimeters is considered suitable.

Distal portion 110 extends from intermediate portion 108 to the distal end 104 of the elongate member 101. Distal portion 110 has a length 118 and a uniform, or substantially uniform, outer diameter 116. Distal portion 110 is flexible, or substantially flexible, such that it can navigate through any curves defined along the length of a scope or sheath and/or within tortuous bodily passages. Distal portion 110 can have any suitable outer diameter 116 and length 118, and skilled artisans will be able to select a suitable outer diameter and length for the distal portion of an elongate member according to a particular embodiment based on various considerations, such as the nature of the bodily passage and/or the inner diameter of the lumen of a scope or sheath through which a probe is intended to be used. It is considered advantageous for distal portion 110 to have an outer diameter 116 that is adapted to be passed through the lumen of a scope or sheath.

The inventor has determined that an outer diameter 116 between about 0.1 millimeters and about 1.0 millimeter is suitable. In addition, the inventor has determined that an outer diameter 116 between about 0.25 millimeters and about 0.75 millimeters is suitable. Furthermore, the inventor has determined that an outer diameter 116 of about, equal to, or substantially equal to, 0.56 millimeters is considered suitable. Moreover, the inventor has determined that an outer diameter 116 about, equal to, or substantially equal to, 0.40 millimeters is considered suitable.

The inventor has also determined that an outer diameter 116 between about 0.01 millimeter and about 0.15 millimeters smaller than the inner diameter of the lumen of a scope or sheath through which a probe is intended to be used is considered suitable. In addition, the inventor has determined that an outer diameter 116 between about 0.025 millimeters and about 0.125 millimeters smaller than the inner diameter of the lumen of a scope or sheath through which a probe is intended to be used is considered suitable. Furthermore, the inventor has determined that an outer diameter 116 between about 0.05 millimeters and about 0.10 millimeter smaller than the inner diameter of the lumen of a scope or sheath through which a probe is intended to be used is considered suitable. Moreover, the inventor has determined that an outer diameter 116 about, equal to, or substantially equal to, 0.05 millimeters smaller than the inner diameter of the lumen of a scope or sheath through which a probe is intended to be used is considered suitable.

The length 118 of distal portion 110 will vary depending on the intended use of probe 100 and on the portion of probe 100 that will be passed through the lumen of a scope or sheath. For example, when the distal end 104 of elongate member 101 is being used within a salivary duct, only the distal portion 110 of elongate member 101 will be passed through the lumen of a scope or sheath. However, while a particular portion of probe 100 has been described as being passed through the lumen of a scope or sheath, other portions of probe 100 are considered suitable to pass through the lumen of a scope or sheath. Skilled artisans will be able to select a suitable portion to pass through the lumen of a scope or sheath based on various considerations, such as the nature of the bodily passage and/or the inner diameter of the lumen of a scope or sheath within which the probe is intended to be used. The inventor has determined that a distal portion 110 having a length 118 that is between about 0.5 centimeters and about 3.5 centimeters greater than the length of the lumen of the sheath and/or scope that the distal portion 110 is being passed through is considered suitable. Also, the inventor has determined that a distal portion 110 having a length 118 that is between about 1.5 centimeters and about 2.5 centimeters greater than the length of the lumen of the sheath and/or scope that the distal portion 110 is being passed through is considered suitable. In addition, the inventor has determined that a distal portion 110 having a length 118 about, equal to, or substantially equal to 1.0 centimeter greater than the length of the lumen of the sheath and/or scope that the distal portion 110 is being passed through is considered suitable. Also, the inventor has determined that a distal portion 110 having a length 118 about, equal to, or substantially equal to 1.5 centimeters greater than the length of the lumen of the sheath and/or scope that the distal portion 110 is being passed through is considered suitable. Moreover, the inventor has determined that a distal portion 110 having a length 118 about, equal to, or substantially equal to 2.0 centimeters greater than the length of the lumen of the sheath and/or scope that the distal portion 110 is being passed through is considered suitable. It is considered advantageous to only pass a small length of a probe distal to the distal end of the sheath and/or scope that a probe is being passed through to ensure that the unsupported portion (e.g., the length of probe disposed distal to the distal end of the sheath and/or scope) is limited to maintain power transferred along the length of the probe by a lithotripter, or other device.

It is considered advantageous to provide a proximal portion 106 that has an outer diameter 112 greater than the outer diameter 116 of distal portion 110 to allow distal portion 110 to be used in bodily passages, or devices, defining a lumen that has a diameter smaller than the outer diameter 112 of proximal portion 106. Furthermore, the structural relationship between proximal portion 106 and distal portion 110 provides more efficient transmission of power along the length of elongate member 101 when lithotripsy is being performed as compared to a probe having a small continuous outer diameter along its length.

It is also considered advantageous to provide a proximal portion 106 that is rigid, or substantially rigid, relative to the distal portion 110 that is flexible, or substantially flexible, to allow distal portion 110 to be navigated through tortuous passages. For example, it is considered advantageous to provide a proximal portion 106 that is relatively rigid relative to a distal portion 110, and a distal portion 110 that is flexible relative to a proximal portion 110.

Elongate member 101 can be formed of any suitable material and manufactured using any suitable method, and skilled artisans will be able to select a suitable material to form an elongate member and method of manufacture for a particular embodiment based on various considerations, such as the desired outer diameter of the proximal portion and/or distal portion of the probe. Example materials considered suitable to form an elongate member include, but are not limited to, biocompatible materials, materials that can be made biocompatible, stainless steel, nickel titanium, cobalt chromium, plastics, polymers, and any other suitable material or combination. The proximal portion 106, intermediate portion 108, and/or distal portion 110 of elongate member 101 can be formed of the same material, or formed of different materials. For example, distal portion 110 can be formed of nickel titanium to provide flexibility, and allowing distal portion 110 to be passed through tortuous passages. An example method of manufacture considered suitable includes, but is not limited to, centerless grinding of a mandrel to form the probes described herein. Another example method of manufacture considered suitable includes forming intermediate portion 108 and distal portion 110 by inserting nickel titanium into a cannula having a tapered distal end.

In the illustrated embodiment, distal portion 110 of the elongate member 101 comprises one or more indicia 111 disposed along its length 118. The one or more indicia 111 can be formed on the outer surface of distal portion 110, or be embedded within the material forming distal portion 110. The one or more indicia 111 can be disposed at equal, or varying, lengths and can be used to determine the amount of elongate member 101 disposed within the lumen of a scope, sheath, and/or a bodily passage. Alternatively, each of the one or more indicia 111 can comprise a raised protuberance extending radially outward from the exterior surface of distal portion 110. The raised protuberance can extend about the entirety of the circumference, or a portion of the circumference, of distal portion 110. Optionally, the one or more indicia 111 can be omitted from inclusion with distal portion 110.

While the distal portion 110 of the elongate member 101 has been illustrated and described as having one or more indicia 111 disposed along its length, any suitable portion of elongate member 101 can include one or more indicia, and skilled artisans will be able to select a suitable portion of an elongate member to include one or more indicia according to a particular embodiment based on various considerations, such as the nature of the bodily passage and/or the inner diameter of the lumen of a scope or sheath within which a probe is intended to be used. Example portions of an elongate member that are considered suitable to include one or more indicia include, but are not limited to, proximal portion 106, and intermediate portion 108. For example, proximal portion can include one or more indicia disposed along its length to determine the length of elongate member 101 disposed within the lumen of a sheath, scope, and/or bodily passage.

Fitting 130 is disposed on the proximal end 102 of the elongate member 101. Fitting 130 provides a mechanism for attaching probe 100 to the handle of a lithotripter allowing the lithotripter to transfer energy to probe 100 when a firing handle is activated. Fitting 130 comprises a tubular member 131 that has a proximal end 132, a distal end 134, a first outer diameter 133, a second outer diameter 135, a first member 136, a second member 138, and defines a lumen 140. The first outer diameter 133 extends from the distal end 134 towards the proximal end 132 to second member 138. The second outer diameter 135 extends between the first member 136 and second member 138. The first member 136 extends radially outward from the proximal end 132 of tubular member 131 and has a third outer diameter 137 that is greater than the second outer diameter 135 of tubular member 131. The second member 138 extends radially outward from tubular member 131, is disposed between the first member 136 and the distal end 134 of tubular member 131, and has a fourth outer diameter 139 that is greater than the second outer diameter 135 of tubular member 131.

Fitting 130 is disposed on the proximal end 102 of elongate member 101 by inserting the proximal end 102 of elongate member 101 through the lumen 140 of fitting 130. Fitting 130 can be attached to elongate member 101 using any suitable method of attachment, and a skilled artisan will be able to select a suitable method to attach a fitting to an elongate member according to a particular embodiment based on various considerations, such as the intended use of the probe. Example methods of attachment between a fitting and an elongate member considered suitable include, but are not limited to, using an adhesive, welding, threading, crimping, using integrated elements, and/or a combination of these methods or any other suitable method. It is considered advantageous to attach fitting 130 to elongate member 101 by threading and/or crimping the tubular member 131 of fitting 130 at one or more locations between the proximal end 132 and distal end 134 of fitting or between first member 136 and the second member 138 at least because it reduces the likelihood of fitting 130 becoming detached, and/or loose, from elongate member 101 during use.

Fitting 130 can be formed of any suitable material, manufactured using any suitable method, and form any suitable structure adapted to attach a probe to a housing, handle, and/or lithotripter. Skilled artisans will be able to select a suitable material to form a fitting, method of manufacture, and structure for a particular embodiment based on various considerations, such as the desired housing, handle, and/or lithotripter to which a probe is intended to be attached. Example materials considered suitable to form a fitting include, but are not limited to, biocompatible materials, materials that can be made biocompatible, stainless steel, nickel titanium, cobalt chromium, plastics, and any other suitable material or combination thereof.

Each of the first outer diameter 133, second outer diameter 135, third outer diameter 137, and fourth outer diameter 139 can have any suitable length, and skilled artisans will be able to select suitable lengths according to a particular embodiment based on various considerations, including the desired housing, handle, and/or lithotripter to which a probe is intended to be attached. Example lengths considered suitable include, but are not limited to, a first outer diameter that is greater than the second outer diameter, a first outer diameter that is equal to, or substantially equal to, the second outer diameter, and a first outer diameter that is less than the second outer diameter. The inventor has determined that a first outer diameter 133 that is greater than the second outer diameter 135 is considered advantageous at least because optimal crimping of fitting 130 to elongate member 101 can be accomplished. This can be accomplished, for example, by providing a fitting 130 that has a tubular member 131 that defines a first thickness along the length of the tubular member 131 that defines the first outer diameter 133 and a second thickness along the length of the tubular member 131 that defines the second outer diameter 135 such that the first thickness is greater than the second thickness.

O-ring 150 is disposed between the second member 138 and the distal end 134 of tubular member 131. O-ring 150 provides a mechanism for dampening the engagement between probe 100 and the handle of a lithotripter when in use. O-ring 150 comprises a body 151 that defines an aperture 152 and an outer diameter 154. The aperture 152 has an inner diameter that is equal to, or less than, the first outer diameter 133 of tubular member 131 so that releasable attachment between O-ring 150 and fitting 130 can be accomplished by a friction fit between the O-ring 150 and fitting 130.

Any suitable O-ring, formed of any suitable material, defining any suitable inner diameter and outer diameter can be utilized, and skilled artisans will be able to select a suitable O-ring, material, inner diameter, and outer diameter for an O-ring according to a particular embodiment based on various considerations, such as the outer diameter of the fitting and/or elongate member. It is considered advantageous to form an O-ring of a flexible, or substantially flexible, material to provide dampening of the engagement between a probe and the handle of a lithotripter when in use.

While fitting 130 and O-ring 150 have been described and illustrated as disposed on elongate member 101, fitting 130 and O-ring 150 can optionally be omitted from probe 100, or alternative structures can be utilized to provide a mechanism to attach a probe 100 to a housing, handle, and/or lithotripter. Skilled artisans will be able to select a suitable structure (e.g., fitting, O-ring) to include with a probe according to a particular embodiment based on various considerations, such as the structure of the housing, handle, or lithotripter to which a probe is intended to be attached. For example, a fitting and an elongate member can be a unitary, integral, component. This can be accomplished, for example, by centerless grinding a fitting, such as those described herein, on the proximal end of an elongate member.

Alternative to the structural arrangement illustrated and described above, an elongate member can define a member that extends outward and away (e.g., radially outward) from the proximal portion about a portion, or the entirety, of the circumference of the proximal portion and along a portion of the length of the proximal portion. It is considered advantageous for the member to be positioned on the proximal end of the elongate member. The member can be an integral portion of the elongate member, or attached to the elongate member using any suitable technique, such as those described herein. In addition, the fitting can define a recess on the proximal end of the fitting (e.g., about the lumen of fitting) that corresponds with, or is complementary to, the structural arrangement of the member disposed on the elongate member. Thus, elongate member has a stepped configuration on the proximal end that is adapted to, or is disposed within, a recess defined by fitting on the fitting proximal end. This structural arrangement is considered advantageous at least because it provides a mechanism for preventing distal advancement of the elongate member beyond a location where the member of the elongate member is disposed within the recess defined by the fitting.

Figure 1A:
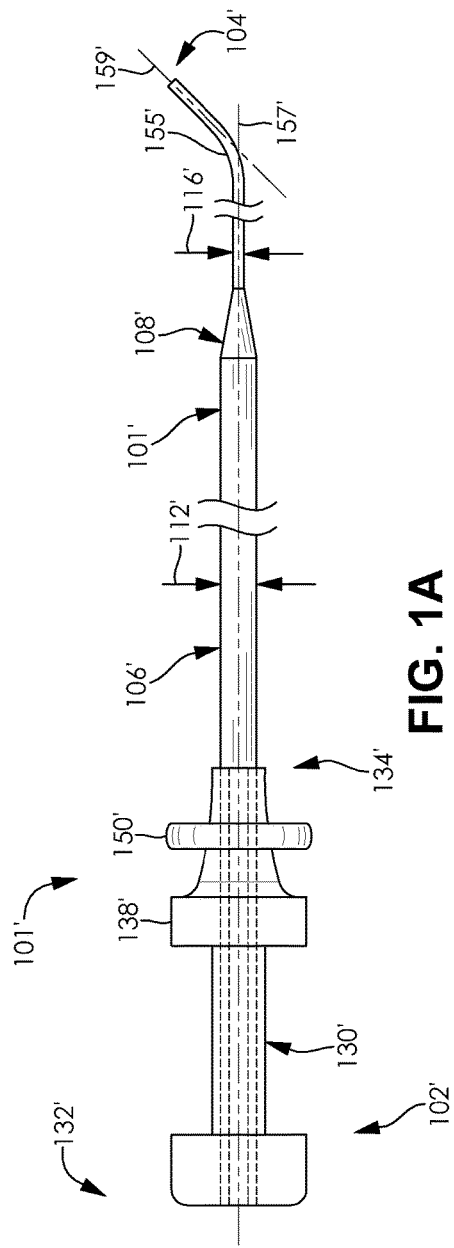
FIG. 1A is a side view of another exemplary probe.

FIG. 1A illustrates another exemplary probe 100' that is similar to probe 100, except as described. Reference numbers in FIG. 1A refer to the same structural element or feature referenced by the same number in FIG. 1, offset by '. Thus, probe 100' comprises an elongate member 101', a fitting 130' disposed on the proximal end 102' of elongate member 101', and an O-ring 150' disposed between the second member 138' the distal end 134' of fitting 130'.

In the illustrated embodiment, elongate member 101' defines an elongate member curve 155' between elongate member distal end 104' and intermediate portion 108'. Elongate member 101' is adapted to move between a curved configuration, as shown in FIG. 1A, to a straight, or substantially straight, configuration, as described in more detail herein. In the straight, or substantially straight, configuration the portion of elongate member 101' that defines elongate member curve 155' is straight, or substantially straight, when it is disposed in a lumen defined by a device (e.g., lumen of scope, lumen of sheath). When free of the lumen, elongate member 101' is biased to the curved configuration. It is considered advantageous to form elongate member 101' of a material that allows torque to be transferred along the length of elongate member 101' at least because this provides a mechanism for rotating elongate member 101' and positioning it at a desired point of treatment.

Elongate member 101' has an elongate member first axis 157' and an elongate member second axis 159' disposed at an angle to elongate member first axis 157'. Elongate member first axis 157' extends along a portion, or the entirety, of elongate member 101' disposed proximal to elongate member curve 155' (e.g., proximal portion 106'). Elongate member second axis 157' extends through elongate member first axis 157', through a portion of elongate member 101' disposed distal to elongate member curve 155' and/or through elongate member distal end 104'.

Elongate member 101' can define any suitable angle between the elongate member first axis 157' and elongate member second axis 159', and skilled artisans will be able to select a suitable angle to define between an elongate member first axis and an elongate member second axis according to a particular embodiment based on various considerations, including the procedure intended to be performed. Example angles considered suitable to define between an elongate member first axis and an elongate member second axis include, but are not limited to, acute angles, obtuse angles, a 45 degree angle, a substantially 45 degree angle, a 90 degree angle, a substantially 90 degree angle, a 135 degree angle, a substantially 135 degree angle, and any other angle considered suitable for a particular application. The inventor has determined that angles that offset the elongate member distal end 104' from the elongate member first axis 157' between about 0.1 millimeters to about 5 millimeters are considered advantageous. The inventor has also determined that angles that offset the elongate member distal end 104' from the elongate member first axis 157' between about 0.5 millimeters to about 3 millimeters are considered advantageous. The inventor has also determined that greater distances are considered advantageous in settings in which the elongate member 101' is used in bodily passages other than the salivary ducts.

Curve 155' can be formed on elongate member 101' using any suitable technique, and skilled artisans will be able to select a suitable technique to form a curve on an elongate member according to a particular embodiment based on various considerations, including the material forming an elongate member. An example technique considered suitable to form a curve on an elongate member includes, but is not limited to, positioning the elongate member in the second curved configuration and then applying heat to the portion of the elongate member length in which it is desired to form a curve such that the curve is incorporated into the material forming the elongate member. Alternative to defining a curve 155', an elongate member can define a bend along the length of elongate member 101'. It is considered advantageous for elongate member 101' to be formed of a material that allows elongate member curve 155' and elongate member distal end 104' to be torqued during treatment at least because this provides a mechanism for positioning elongate member distal end 104' at a point of treatment.

While curve 155' has been illustrated as defined between elongate member distal end 104' and intermediate portion 108', a curve can be defined along any suitable portion, or the entirety, of the length of an elongate member. Skilled artisans will be able to select a suitable portion of an elongate member length to define a curve according to a particular embodiment based on various considerations, including the material forming the elongate member. Example portions of an elongate member length considered suitable to define a curve include, but are not limited to, defining a curve between an elongate member proximal end and an elongate member distal end, between an elongate member distal end and an intermediate portion, between an elongate member distal end and a proximal portion, between an elongate member distal end and a fitting, between a fitting and an intermediate portion, along an intermediate portion, and any other portion of an elongate member length considered suitable for a particular application.

The inclusion of curve 155' on elongate member 101' is considered advantageous at least because it provides a mechanism for advancing probe 100' through the tortuous anatomy of a bodily passage and towards a point of treatment. For example, when probe 100' is passed through a lumen defined by a scope, probe 100' can be advanced through the tortuous anatomy of the bodily passage without requiring manipulation of the scope, which may result in the optics becoming obstructed by the wall of the bodily passage, or otherwise.

Figure 2:
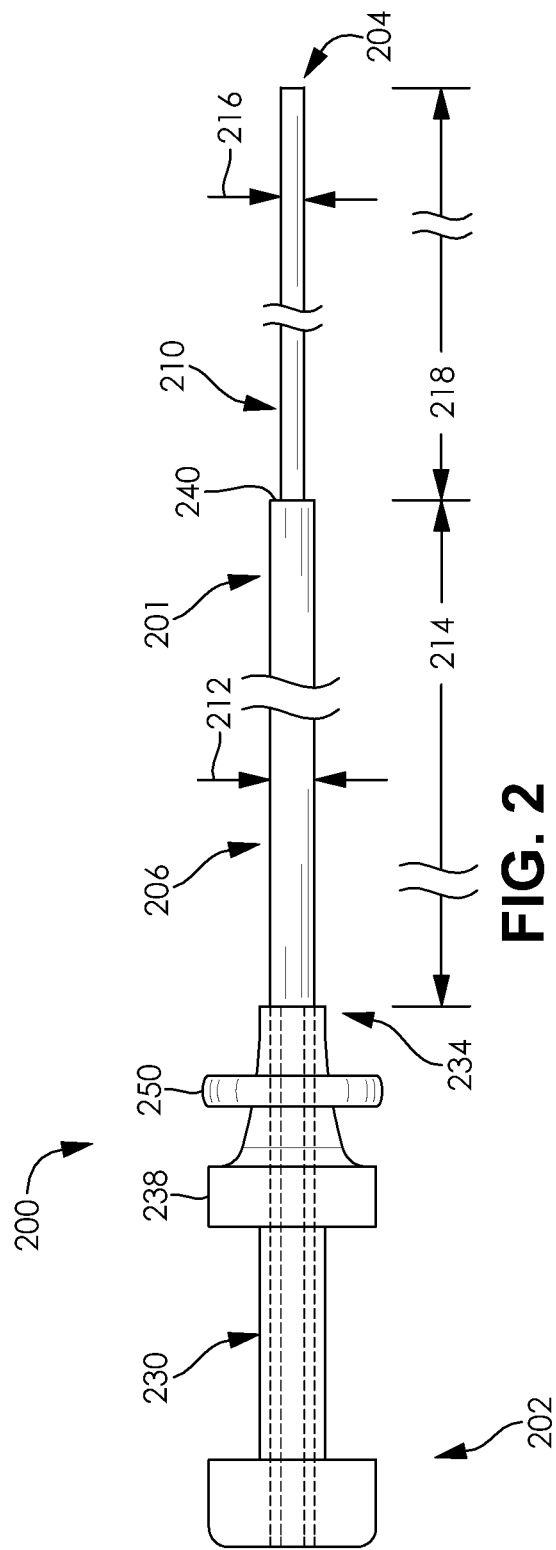
FIG. 2 is a side view of another exemplary probe.

FIG. 2 illustrates another exemplary probe 200 that is similar to probe 100, except as described. Reference numbers in FIG. 2 refer to the same structural element or feature referenced by the same number in FIG. 1, offset by 100. Thus, the probe 200 comprises an elongate member 201, a fitting 230 disposed on the proximal end of elongate member 201, and an O-ring 250 disposed between the second member 238 the distal end 234 of fitting 230.

In this embodiment elongate member 201 defines a shoulder 240 instead of an intermediate portion, such as intermediate portion 108 illustrated in FIG. 1. Thus, elongate member 201 comprises a proximal end 202, distal end 204, proximal portion 206, distal portion 210, and defines shoulder 240. Proximal portion 206 extends from the proximal end 202 to the distal portion 210 and has a length 214 that extends distal to fitting 230. Proximal portion 206 has a uniform, or substantially uniform, outer diameter 212, is rigid, or substantially rigid, and can have any suitable outer diameter 212 and length 214. A skilled artisan will be able to select a suitable outer diameter 212 and length 214 for the proximal portion 206 of an elongate member 201 according to a particular embodiment based on various considerations, such as the nature of the bodily passage and/or the inner diameter of the lumen of a scope or sheath within which the probe is intended to be used, the amount of energy desired to be transmitted to the distal end of the elongate member, and the desired flexibility of the elongate member.

Distal portion 210 extends from proximal portion 206 to the distal end 204 of elongate member 201 and has a length 218 and a uniform, or substantially uniform, outer diameter 216. Distal portion 210 is flexible, or substantially flexible, and can have any suitable outer diameter 216 and length 218. A skilled artisan will be able to select a suitable outer diameter 216 and length 218 for the distal portion 210 of an elongate member according to a particular embodiment based on various considerations, such as the nature of the bodily passage and/or the inner diameter of the working channel of a scope or lumen of a sheath within which the probe is intended to be used, the amount of energy desired to be transmitted to the distal end of the elongate member, and the desired flexibility of the elongate member.

Elongate member 201 defines shoulder 240 at a location between the proximal end 202 and the distal end 204 of elongate member 201 that reduces the outer diameter 212 of proximal portion 206 to the outer diameter 216 of distal portion 210. Thus, the outer diameter 212 of proximal portion 206 is greater than the outer diameter 216 of distal portion 210. It is considered advantageous to define a shoulder 240 between the proximal end 202 and the distal end 204 of an elongate member 201 to provide a mechanism for preventing advancement of probe 200 distally through the lumen of a probe or sheath, beyond shoulder 240 when the outer diameter 212 of proximal portion 206 is greater than the inner diameter of the lumen of the scope or sheath.

Figure 3:
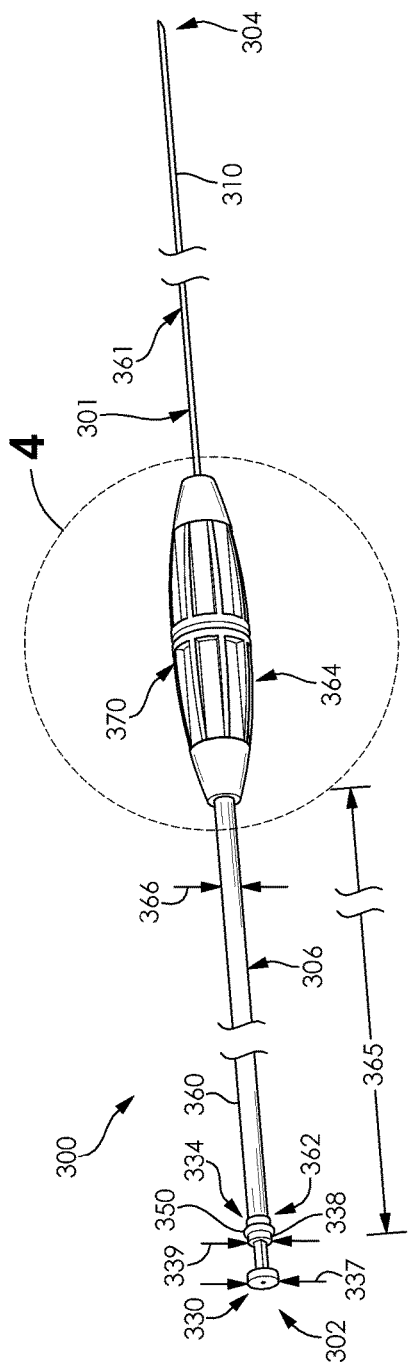
FIG. 3 is a perspective view of another exemplary probe with an associated elongate tubular member and handle.
Figure 4:
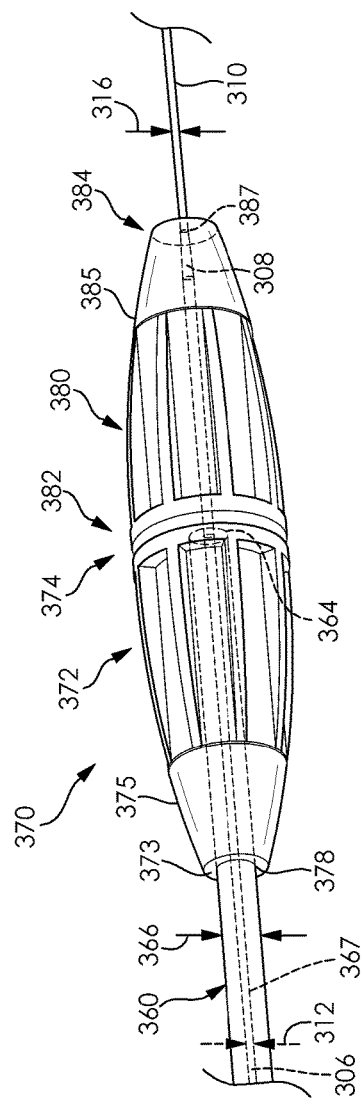
FIG. 4 is a magnified view of area 4 indicated in FIG. 3.

FIGS. 3 and 4 illustrate an exemplary probe 300. Reference numbers in FIGS. 3 and 4 refer to the same structural element or feature referenced by the same number in FIG. 1, offset by 200. Probe 300 comprises an elongate member 301, a fitting 330 disposed on the proximal end of elongate member 301, an O-ring 350 disposed between the second member 338 and the distal end 334 of fitting 330, an elongate tubular member 360, and handle 370. The elongate member 301, fitting 330, and O-ring 350 are similar to the elongate member 101, fitting 130, and O-ring 150 described with respect to FIG. 1, except as described.

In this embodiment, elongate tubular member 360 and handle 370 are disposed along a portion of the length of elongate member 301. Handle 370 has a first configuration and a second configuration. In the first configuration, the elongate tubular member 360 and handle 370 are slidably disposed along a portion of the length of elongate member 301. In the second configuration, the elongate tubular member 360 and handle 370 are releasably attached to elongate member 301. The inclusion of an elongate tubular member 360 and handle 370 is considered advantageous at least because it provides a user with the ability to have fine motor control over the probe 300 during the performance of lithotripsy and provides a mechanism to prevent the distal end 304 of elongate member 301 from being inserted beyond a desired point into a scope, sheath, and/or bodily passage.

Elongate member 301 comprises a proximal end 302, distal end 304, proximal portion 306, intermediate portion 308, and distal portion 310. Elongate tubular member 360 is slidably disposed over a length of elongate member 301 and comprises a proximal end 362 and a distal end 364. Elongate tubular member 360 has a length 365, an outer diameter 366, and defines a lumen 367 that forms an opening at the proximal end 362 and an opening at the distal end 364. The proximal end 362 of elongate tubular member 360 is disposed adjacent the distal end 334 of fitting 330 and the distal end 364 of elongate tubular member 360 is disposed proximal to intermediate portion 308 of elongate member 301. Alternatively, the distal end 364 of elongate tubular member 360 can be disposed at any point along the length of elongate member 301 (e.g., at, or near, intermediate portion 308). The lumen 367 of elongate tubular member 360 has an inner diameter that is greater than the outer diameter 312 of proximal portion 306 to allow for slidable engagement between the elongate tubular member 360 and elongate member 301 when the elongate tubular member 360 is disposed along a portion of the length of elongate member 301.

While elongate tubular member 360 has been described as having a particular length 365, elongate tubular member 360 can have any suitable length, and skilled artisans will be able to select a suitable length for an elongate tubular member according to a particular embodiment based on various considerations, such as the desired positioning of handle 370 along the length of elongate member 301. Example lengths considered suitable for the elongate tubular member 360 include lengths that position the distal end 364 of elongate tubular member 360 between proximal portion 306 and intermediate portion 308, along the length of intermediate portion 308, between intermediate portion 308 and distal portion 310, or along the length of distal portion 310 when the proximal end 362 of elongate tubular member 360 is disposed adjacent to the distal end 334 of fitting 330. It is considered advantageous to provide an elongate tubular member 360 with a length 365 that positions handle 370 at least over intermediate portion 308 of probe 300 when the proximal end 362 of elongate tubular member 360 is positioned adjacent to the distal end 334 of the fitting 330.

FIG. 5 illustrates an exploded view of the elongate tubular member 360 and handle 370 free of elongate member 301. Handle 370 comprises a first portion 372 and a second portion 380. First portion 372 is attached to the distal end 364 of elongate tubular member 360 and comprises a proximal end 373, distal end 374, shaft 375, threaded portion 376, and one or more projections 377.

Shaft 375 extends from the proximal end 373 towards the distal end 374 to threaded portion 376. The body 371 of first portion 372 defines threaded portion 376, which extends from the distal end of shaft 375 towards distal end 374 and is disposed between shaft 375 and the one or more projections 377. Threaded portion 376 comprises a circumferentially outwardly extending helical ridge.

The one or more projections 377 extend about the entirety, or a portion, of the circumference of the distal end of threaded portion 376 to the distal end 374 of first portion 372. The one or more projections 377 form a collet configuration that extends from the distal end of threaded portion 376 to the distal end 374 of first portion 372. The one or more projections 377 can optionally comprise one or more inwardly extending teeth and/or ridges on a portion, or the entirety, of the interior surface of the one or more projections 377 to assist with attaching handle 370 to the elongate member 301.

The body 371 of first portion 372 defines an aperture 378 that extends through shaft 375 and threaded portion 376 from an opening at the proximal end 373 of first portion 372 to an opening at the distal end of threaded portion 376. Aperture 378 provides access through the length of first portion 372 and has a diameter 379 that is greater than the outer diameter 366 of elongate tubular member 360 and the outer diameter 312 of the proximal portion 306 of elongate member 301. Alternatively, a proximal portion of aperture 378 can have a diameter 379 that is greater than the outer diameter 366 of elongate tubular member 360 a distal portion of aperture 378 such that a ridge is defined within the aperture 378. This structural arrangement is considered advantageous at least because it provides a mechanical stop to distal advancement of the distal end 364 of elongate tubular member 360 within aperture 378. Thus, distal end 364 can be disposed at the ridge defined within aperture 378.

The first portion 372 of handle 370 is attached to the distal end 364 of elongate tubular member 360 using any suitable method of attachment, and skilled artisans will be able to select a suitable method of attachment according to a particular embodiment based on various considerations, such as the intended use of probe 300. Examples of suitable methods of attachment include, but are not limited to, using an adhesive, welding, and/or using integrated components.

The second portion 380 of handle 370 comprises a proximal end 382, distal end 384, shaft 385, and a body 381 that defines a recess 386 and an aperture 387. Shaft 385 extends from the proximal end 382 to the distal end 384 of second portion 380. Recess 386 extends from the proximal end 382 of second portion 380 into shaft 385 towards the distal end 384 to base 388. The interior wall 390 of body 381 defines a threaded portion 389, which comprises a circumferentially outwardly extending helical ridge that extends from the proximal end 382 towards the distal end 384 of second portion 380. Threaded portion 389 of second portion 380 complements threaded portion 376 of first portion 372 such that releasable attachment between the first portion 372 and second portion 380 can be accomplished.

Recess 386 has a tapered configuration from the distal end of threaded portion 389 to base 388 and is adapted to receive the one or more projections 377 of first portion 372. Aperture 387 extends from an opening on base 388 of recess 386 to an opening on the distal end 384 of second portion 380. Aperture 387 has a diameter that is greater than the outer diameter 312 of proximal portion 306 of elongate member 301. Alternatively, aperture 387 can comprise any suitable diameter. For example, aperture 387 can have a diameter that is greater than the outer diameter of 308, or outer diameter of 310, depending on the placement of the handle 370 along elongate member 306. Thus, any aperture of a handle can have a diameter that is equal to, substantially equal to, or greater than the portion of an elongate member that is disposed through the aperture.

In use, prior to, during, or subsequent to probe 300 being attached to a handle of a lithotripter using a sleeve, or other means of attachment, the elongate tubular member 360 and handle 370 can be releasably attached to elongate member 301. This can be accomplished by inserting the distal end 304 of elongate member 301 through the lumen 367 of elongate tubular member 360, aperture 378 of first portion 372, and aperture 387 of second portion 380. To releasably attach elongate tubular member 360 and handle 370 along a portion of the length of elongate member 301, a user moves handle 370 from its first configuration to its second configuration. In the first configuration threaded portion 376 of first portion 372 is free of threaded portion 389 of second portion 380 and elongate tubular member 360 and handle 370 are slidably disposed along the length of elongate member 301. In the first configuration, the one or more projections 377 define a first inside diameter that is greater than, or slightly greater than, the outer diameter 312 of the proximal portion 306 of elongate member 301, or greater than the outer diameter 316 of the distal portion 310 of elongate member 301, allowing elongate tubular member 360 and first portion 372 to be slidable along the length of elongate member 301. Alternatively, the one or more projections 377 can define a first inside diameter that is greater than, or slightly greater than, the outer diameter of the intermediate portion 308.

In the second configuration, threaded portion 376 of first portion 372 is engaged with threaded portion 389 of second portion 380 such that the one or more projections 377 are disposed within the tapered configuration of recess 386 of second portion 380, releasably attaching elongate tubular member 360 and handle 370 to elongate member 301. Thus, the first portion 372 is releasably attached to the second portion 380. The tapered configuration of recess 386 compresses a portion, or the entirety, of the one or more projections 377 against the exterior surface of elongate member 301 to engage and/or lock handle 370 in place along the length of elongate member 301. Thus, in the second configuration, the one or more projections 377 define a second inside diameter that is equal to, or substantially equal to, the outer diameter of elongate member 301.

Elongate tubular member 360 and handle 370 can advantageously be removed from elongate member 301 and/or adjusted along the length of elongate member 301 as desired by a user. To accomplish adjusting the position of elongate tubular member 360 and handle 370 a user moves handle 370 from the second configuration to the first configuration, or a position between the second configuration and the first configuration. Subsequently, the user slides the elongate tubular member 360 and handle 370 to a desired position along the length of elongate member 301 and moves the handle 370 back to the second configuration. To accomplish removing the elongate tubular member 360 and handle 370 from elongate member 301 a user moves the handle 370 from the second configuration to the first configuration, or a position between the second configuration and the first configuration, and slides the elongate tubular member 360 and handle 370 off of elongate member 301.

Elongate tubular member 360 and handle 370 can be formed of any suitable material, and skilled artisans will be able to select an appropriate material according to a particular embodiment based on various considerations, such as the intended use of the probe. Example materials considered suitable include, but are not limited to, metals, stainless steel, nickel titanium, cobalt chromium, plastics, polymers, biocompatible materials, materials that can be made biocompatible, or variations thereof. In addition, while first portion 372 has been described as having threaded portion 376 and second portion 380 has been described as having threaded portion 389, other methods of providing releasable attachment between first portion 372 and second portion 380 are considered suitable, and skilled artisans will be able to select an appropriate method of attachment based on various considerations, such as the outer diameter of the probe being utilized. Example methods of attachment considered suitable between first portion and second portion include, but are not limited to, providing a snap fit, pin vice, and/or a Morse taper.

Optionally, elongate member 301 can comprise one or more indicia (e.g., markers) disposed along its length, which correlate with a length of elongate member 301 that extends distal and/or proximal to the one or more indicia. Any suitable form of measurement can be utilized to indicate the length of elongate member 301 that is disposed distal and/or proximal to the one or more indicia, and skilled artisans will be able to select a suitable form of measurement based on various considerations, such as the bodily passage in which the probe will be used. The one or more indicia can be embedded within, and/or disposed on the exterior surface of elongate member 301. Alternatively, each of the one or more indicia can comprise a raised protuberance extending radially outward from the exterior surface of elongate member 301. The raised protuberance can extend about the entirety of the circumference, or a portion of the circumference, of elongate member 301. The inclusion of a raised protuberance is considered advantageous at least because it provides a user with tactile feedback as to the disposition of handle 370 along the length of elongate member 301 as it is being releasably attached to elongate member 301, allowing the user to releasably attached handle 370 at a particular location along the length of elongate member 301. To assist with positioning handle 370 at a particular location along the length of elongate member 301, handle 370 can optionally comprise one or more recesses adapted to receive one of the one or more raised protuberances. The one or more recesses can circumferentially extend around the entirety, or a portion, of the interior surface of aperture 378 of first portion 372 and/or aperture 387 of second portion 380.

Elongate member 301 can also optionally comprise a roughened surface disposed along the entirety, or a portion, of its length. The inclusion of a roughened surface along the entirety, or a portion, of the length of elongate member 301 is considered advantageous at least because it decreases the likelihood of handle 370 sliding from its position during use. The roughened surface can be accomplished using any suitable method, and skilled artisans will be able to select a suitable method according to a particular embodiment based on various considerations, such as the desired roughness to be provided on the entirety, or a portion, of the length of elongate member. Example methods considered suitable for producing a roughened surface along the entirety, or a portion, of the length of elongate member 301 include, but are not limited to, grit blasting, sanding, and/or etching.

In use, handle 370 advantageously provides a user with fine motor control of probe 300 and tactile feedback relating to the treatment area and/or bodily passage. Fine motor control is considered advantageous at least because it allows a user to properly position the distal end 304 of elongate member 301 prior to activating a handle of a lithotripter. For example, when a stone is being fragmented for removal from a salivary duct, handle 370 provides a user with the ability to finely control the advancement of elongate member 301 and provides tactile feedback as to when the distal end 304 of elongate member 301 is in contact with a stone.

While elongate tubular member 360 and/or handle 370 have been described and illustrated as being used in combination with elongate member 301, elongate tubular member 360 and/or handle 370 can be used in combination with any suitable elongate member. A skilled artisan will be able to select a suitable elongate member to use in combination with elongate tubular member 360 and/or handle 370 based on various considerations, such as the bodily passage in which the elongate member will be used. Example elongate members considered suitable for use in combination with elongate tubular member 360 and/or handle 370 include, but are not limited to, elongate member 101, elongate member 101', elongate member 201, and any other suitable elongate member, such as an elongate member with a continuous, or substantially continuous, outer diameter along its length.

Optionally, the proximal portion 306 of elongate member 301 can include a radially outwardly extending collar disposed along its length that prevents elongate tubular member 360 and/or handle 370 from being attached to elongate member 301 at a location proximal to the collar. Thus, the collar provides a mechanical stop to the proximal progression of elongate tubular member 360 and/or handle 370 when it is being attached to elongate member 301. The collar can comprise a separate element that is slidably disposed along the length of elongate member 301, or be integral with elongate member 301. If the collar is integral with elongate member 301, the collar has an outer diameter that is less than the outer diameter 337 of the first member 336 and the outer diameter 339 of the second member 338 of fitting 330 to allow for attachment of probe 300 to a lithotripter.

Furthermore, while a particular handle 370 has been described and illustrated as disposed along the length of elongate member 301, any suitable structure can be used to provide a user with fine motor control, and skilled artisans will be able to select a suitable structure to use with an elongate member according to a particular embodiment based on various considerations, including the bodily passage within which an elongate member is intended to be used. Example alternative structures considered suitable to include with an elongate member include, but are not limited to, a control handle such as any of those described in U.S. Provisional Patent Application No. 61/533,190, filed Sep. 10, 2011, and co-pending U.S. patent application Ser. No. 13/608,002, filed Sep. 10, 2012, each of which is hereby incorporated by reference in its entirety, and any other suitable structure.

Optionally, elongate tubular member 360 can be omitted and handle 370 can be used independent of elongate tubular member 360, as illustrated in FIG. 5A. As shown in FIG. 5A, a probe 300' comprises an elongate member 301' having a proximal portion 306', an intermediate portion 308', and a distal portion 310'. Handle 370' is releasably attached along the length of elongate member 301' and is in the second configuration. In the illustrated embodiment, probe 300' does not include an elongate tubular member, such as elongate tubular member 360, such that handle 370' can be used independently and be positioned at any suitable location along the length of elongate member 301'.

Any of the elements, features, and/or structural arrangements described herein with respect to any probe, handle, and/or elongate tubular member can be combined in any suitable manner, and skilled artisans will be able to select a suitable element, feature, and/or structural arrangement for a probe, handle, and/or elongate tubular member according to a particular embodiment based on various considerations, such as the desired bodily passage within which a probe is intended to be deployed.

Figure 6:
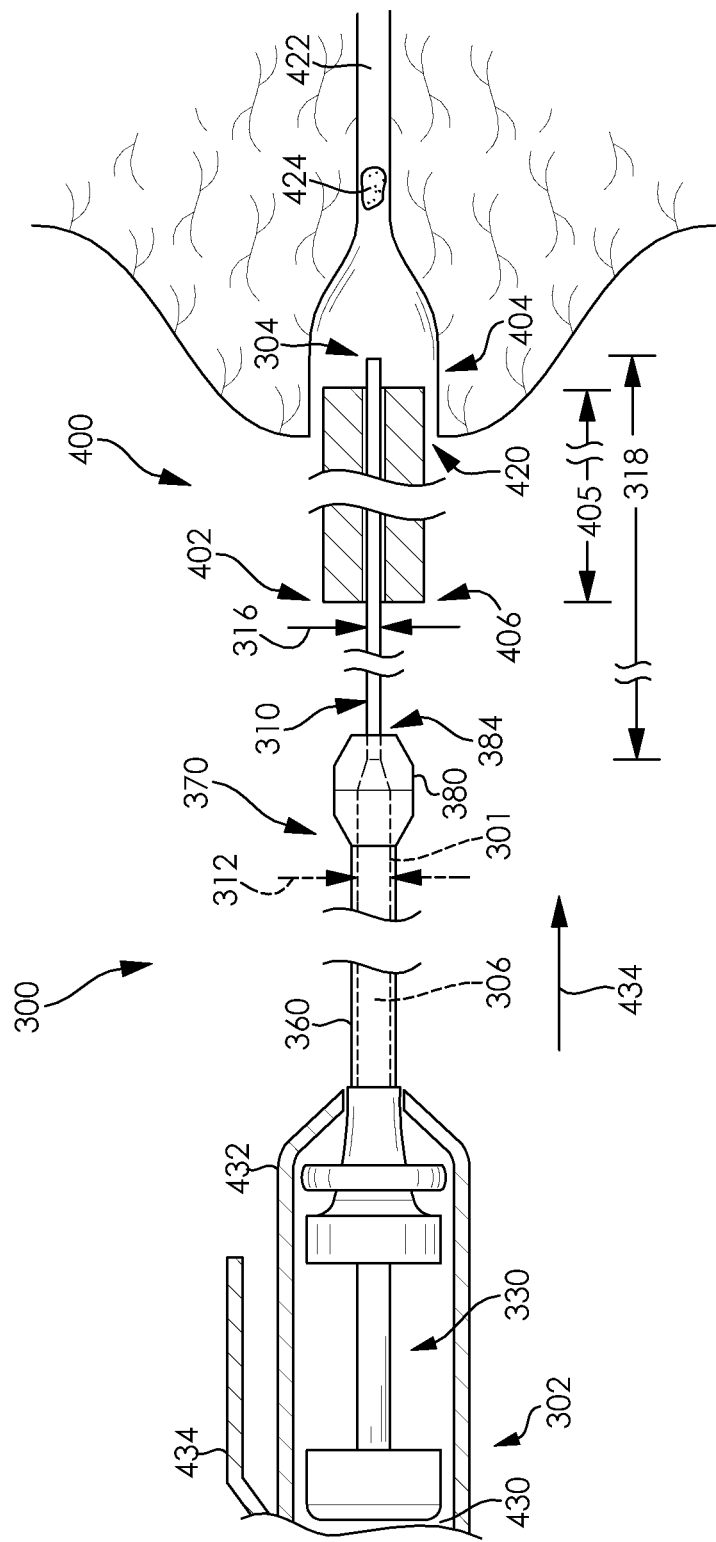
FIG. 6 is a partial sectional view of an exemplary probe and sheath partially disposed in a bodily passage.

FIG. 6 illustrates probe 300 and sheath 400 partially disposed in the opening 420 (e.g., papilla) of a salivary duct 422 that has a stone 424 disposed in its length. The probe 300 is similar to that described above with respect to FIG. 3, except as described. While a salivary duct has been described and illustrated as having a stone disposed in its length, any of the probes, elongate tubular members, and handles described herein can be used in any suitable bodily passage, such as a portion of the urinary tract, and skilled artisans will be able to select a suitable probe, elongate tubular member, and/or handle for use in a particular bodily passage based on various considerations, such as the location of the stone within the bodily passage.

The sheath 400 advantageously allows for the introduction of treatment devices into the salivary duct 422 and comprises a proximal end 402, a distal end 404, length 405, and defines a lumen 406 that extends between an openings at the proximal end 402 and distal end 404. The sheath 400 can be formed out of any suitable material and can have any suitable length, and skilled artisans will be able to select a suitable sheath 400 based on various considerations, such as the bodily passage in which the sheath will be disposed. The inventor has determined that sheaths having a length between about 0.5 centimeters to about 7.0 centimeters are suitable. In addition, the inventor has determined that sheaths having a length between about 1.0 centimeter to about 5.0 centimeters are suitable. For example, the inventor has determined that sheaths having a length about, equal to, or substantially equal to, 1.0 centimeter are suitable for use in the parotid ducts or submandibular ducts. Furthermore, the inventor has determined that sheaths having a length about, equal to, or substantially equal to, 5.0 centimeters are suitable for use in the submandibular ducts or submandibular ducts.

While a sheath 400 has been illustrated in FIG. 6, other various devices can be utilized in combination with the probes described herein. For example, alternative to using a sheath, a scope defining at least one lumen can be used in combination with the probes described herein. No matter the device used in combination with the probes described herein, the lumen 406 of the sheath 400, or the lumen (e.g., working channel) of a scope, or other device, can have any suitable inner diameter, and skilled artisans will be able to select a suitable device according to a particular embodiment based on various considerations, such as the outer diameter of the probe being used. The inventor has determined that sheaths, or scopes, defining a lumen having an inner diameter between about 0.1 millimeters to about 1.1 millimeters are suitable. In addition, the inventor has determined that sheaths, or scopes, defining a lumen having an inner diameter between about 0.35 millimeters to about 0.85 millimeters are suitable. Furthermore, the inventor has determined that a sheath, or scope, defining a lumen having an inner diameter about, equal to, or substantially equal to, 0.65 millimeters is suitable. Moreover, the inventor has determined that a sheath, or scope, defining a lumen having an inner diameter about, equal to, or substantially equal to, 0.45 millimeters is suitable.

Probe 300 is attached to lithotripter 430 by attaching sleeve 432 over fitting 330. Attachment of the sleeve 432 to the lithotripter 430 can be accomplished using any suitable method, and skilled artisans will be able to select a suitable method of attachment based on various considerations, such as the type of lithotripter being used. Example methods of attachment considered suitable include, but are not limited to, using one or more threaded components, a snap fit, or a friction fit.

Distal portion 310 of elongate member 301 has a length 318 that is greater than the length 405 of sheath 400 to allow for the distal end 304 of elongate member 301 to extend past the distal end 404 of sheath 400. Positioning the distal end 304 of elongate member 301 beyond the distal end 404 of sheath 400 can be accomplished by a user placing a distal force, indicated by arrow 434, on a portion of lithotripter 430, handle 370, and/or a portion of probe 300. It is considered advantageous to place the distal force on handle 370 at least to provide tactile feedback while probe is in use or being passed through a bodily passage. As described above, distal portion 310 is flexible, or substantially flexible, which allows it to be advanced through tortuous passages using the lumen 406 of sheath 400 to reinforce its position.

As the distal end 304 of elongate member 301 is passed through the lumen 406 of sheath 400, the distal end 384 of the second portion 380 of handle 370 acts as a mechanical stop by interacting with the proximal end 402 of sheath 400. This advantageously prevents inadvertent advancement of elongate member 301 through the lumen 406 of sheath 400 beyond the position of handle 370. Thus, only the length of elongate member 301 positioned distal to handle 370 can be disposed through the lumen 406 of the sheath 400 and into the salivary duct 422.

In use, the distal end 304 of elongate member 301 is advanced towards stone 424 until the distal end 304 contacts stone 424. Subsequently, the firing handle 434 of lithotripter 430 is activated to transmit energy provided by an energy source (e.g., $CO_2$ cartridge) through elongate member 301 and to stone 424 so that it can be fragmented and removed from the salivary duct 422 using any suitable medical device, such as an irrigation device, suction device, graspers, forceps, and/or baskets.

Figure 7:
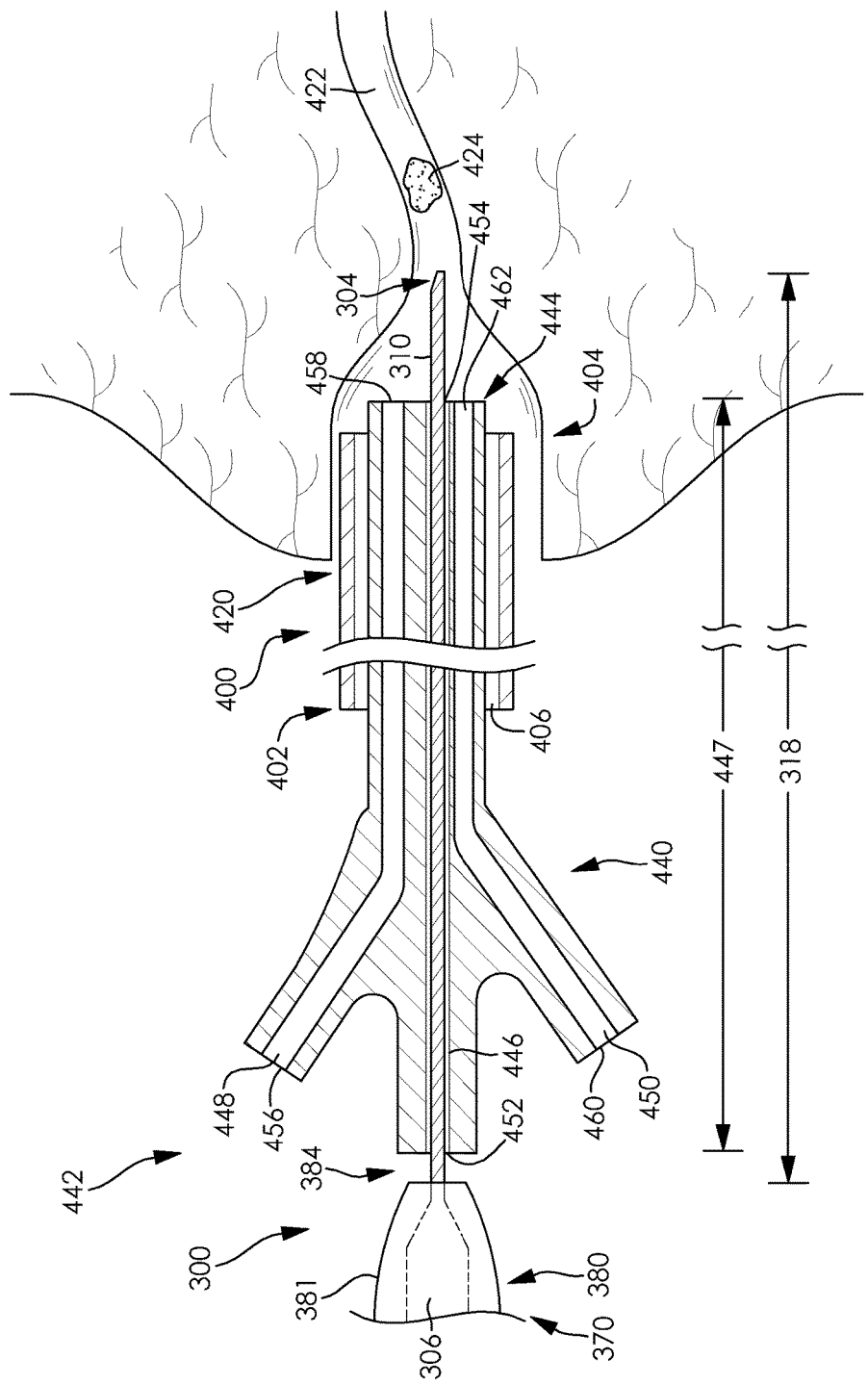
FIG. 7 is a partial cross sectional view of an exemplary probe, sheath, and scope partially disposed in a bodily passage.

FIG. 7 illustrates probe 300, sheath 400, and scope 440 partially disposed in the opening 420 (e.g., papilla) of a salivary duct 422 that has a stone 424 disposed in its length. In the illustrated embodiment, probe 300 is disposed through a first lumen 446 defined by scope 440. Sheath 400 and probe 300 are similar to that described above with respect to FIG. 6, except as described below. Reference numbers in FIG. 7 refer to the same structural element or feature referenced by the same number in FIG. 6. While a salivary duct has been described and illustrated as having a stone disposed in its length, any of the probes, elongate tubular members, and handles described herein can be used in any suitable bodily passage, such as a portion of the urinary tract, and skilled artisans will be able to select a suitable probe, elongate tubular member, and/or handle for use in a particular bodily passage based on various considerations, such as the location of the stone within the bodily passage. While sheath 400 has been illustrated, it is considered optional and can be omitted (e.g., omitted from the methods described herein).

Scope 440 comprises a proximal end 442, a distal end 444, and defines a first lumen 446, second lumen 448, and passageway 450. The first lumen 446 extends between an opening 452 at the proximal end 442 and an opening 454 at the distal end 444 and has a length 447. The first lumen 446 (e.g., the working channel of the scope) is adapted to receive a length of probe 300. The second lumen 448 extends between an opening 456 at the proximal end 442 and an opening 458 at the distal end 444. Passageway 450 extends between an opening 460 at the proximal end 442 and an opening 462 at the distal end 444. The second lumen 448 and passageway 450 are adapted to receive any suitable material, structure, and/or device, and skilled artisans will be able to select a suitable material, structure, and/or device to pass through a lumen and/or passageway of a scope according to a particular embodiment based on various considerations, such as the bodily passage within which the distal end of a scope is intended to be used. Example materials, structures, and devices considered suitable to pass through second lumen 448 and/or passageway 450 include, but are not limited to, an irrigation device, suction device, graspers, forceps, basket, light source, optic source, optical fiber, camera, chip-in-tip fiber optics, a probe, such as any of those described herein, and materials used to flush and/or irrigate a bodily passage. For example, second lumen 448 can be adapted to provide irrigation to salivary duct 422 such that the salivary duct 422 distends relative to its normal structural arrangement and passageway 450 can be adapted to pass optics (e.g., camera, chip-in-tip fibers) and/or light sources (e.g., optical fiber) through lumen 450.

Scope 440 can be formed out of any suitable material, can have any suitable length, and any suitable number of lumens, and skilled artisans will be able to select a suitable scope based on various considerations, such as the bodily passage within which a probe is intended to be used. In addition, while a particular structure has been illustrated and described with respect to scope 440, a scope having any suitable structure capable of providing a lumen adapted to receive a length of a probe is considered suitable. Skilled artisans will be able to select a suitable structure for a probe according to a particular embodiment based on various considerations, such as the bodily passage within which a probe is intended to be used. For example, the distal end of a scope can be formed of a rigid, substantially rigid, flexible, or substantially flexibly material, and/or form one or more curves along its length such that it can be navigated through tortuous bodily passages.

Scope 440 extends through the lumen 406 of sheath 400 such that the distal end 444 of scope is positioned distal to the distal end 404 of sheath 400. Distal portion 310 of elongate member 301 has a length 318 that is greater than the length 447 of the first lumen 446 to allow the distal end 304 of elongate member 301 to extend past the distal end 444 of scope 440. As the distal end 304 of elongate member 301 is passed through the first lumen 446 of scope 440, the distal end 384 of the second portion 380 of handle 370 acts as a mechanical stop by interacting with the proximal end 442 of scope 440. This advantageously prevents inadvertent advancement of elongate member 301 through the first lumen 446 beyond the position of distal end 384. Thus, only the length of elongate member 301 positioned distal to distal end 384 can be disposed through the first lumen 446 of the scope 440 and into the salivary duct 422. In use, it is considered advantageous to maintain a clearance between the distal end 384 of the second portion 380 of handle 370 and the proximal end 442 of scope 440 to prevent reducing the power being transmitted along the length of probe 300.

In use, the distal end 304 of elongate member 301 is advanced towards stone 424 until the distal end 304 contacts stone 424. Subsequently, the firing handle of lithotripter is activated to transmit energy provided by an energy source (e.g., $CO_2$ cartridge) through elongate member 301 and to stone 424 so that it can be fragmented and removed from the salivary duct 422 using any suitable medical device, such as an irrigation device, suction device, graspers, forceps, and/or baskets.

Figure 7A:
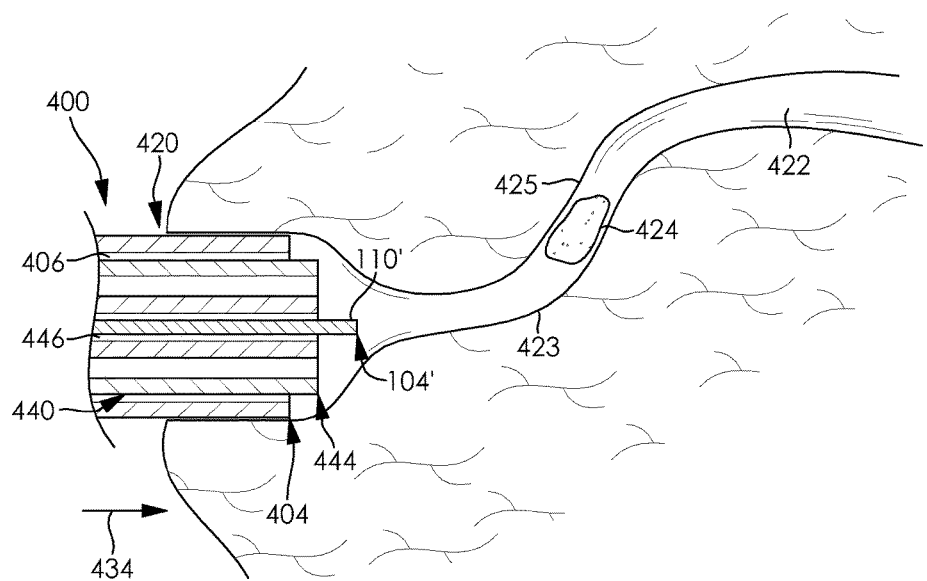
FIG. 7A is a cross sectional view of the distal end of the exemplary probe illustrated in FIG. 1A and the sheath and scope illustrated in FIG. 7 partially disposed in a bodily passage. The probe is in a first straight configuration.
Figure 7B:
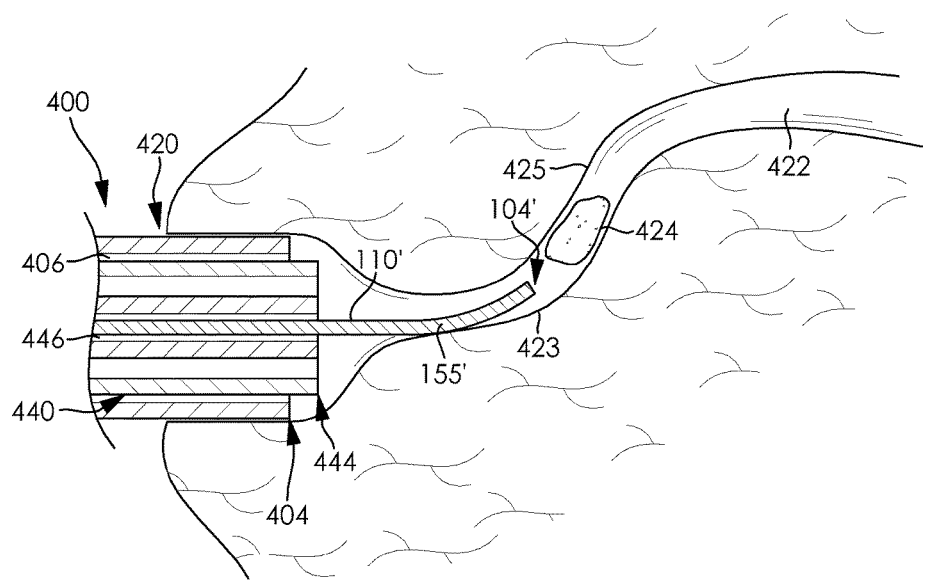
FIG. 7B is a cross sectional view of the distal end of the exemplary probe illustrated in FIG. 1A and the sheath and scope illustrated in FIG. 7 partially disposed in a bodily passage. The probe is in a second curved configuration.

FIGS. 7A and 7B are similar to FIG. 7, except as described below. In the illustrated embodiment, alternative to elongate member 301 being utilized, elongate member 101' is utilized and disposed through a first lumen 446 defined by scope 440. Elongate member 101' is similar to that described above with respect to FIG. 1A and sheath 400 and scope 440 are similar to that described above with respect to FIG. 7, except as described below. Reference numbers in FIGS. 7A and 7B refer to the same structural element or feature referenced by the same number in FIG. 1A and FIG. 7. Thus, elongate member 101' comprises a proximal end (not shown), distal end 104' and defines a curve 155'.

In the illustrated embodiment, salivary duct 422 has a stone 424 disposed in its length beyond a curve 423 defined by the salivary duct wall 425. While a salivary duct has been described and illustrated as having a stone disposed in its length, any of the probes, elongate tubular members, and handles described herein can be used in any suitable bodily passage, such as a portion of the urinary tract, and skilled artisans will be able to select a suitable probe, elongate tubular member, and/or handle for use in a particular bodily passage based on various considerations, such as the location of the stone within the bodily passage.

In the illustrated embodiment, sheath 400 is partially disposed in the opening 420 (e.g., papilla) of salivary duct 422 such that sheath distal end 404 is disposed within the salivary duct 422. Scope 440 extends through the lumen 406 of sheath 400 such that the distal end 444 of scope is positioned distal to the distal end 404 of sheath 400. Distal portion 110' of elongate member 101' has a length that is greater than the length of the first lumen 446 of scope 440 to allow the distal end 104' of elongate member 101' to extend past the distal end 444 of scope 440.

As illustrated in FIG. 7A, elongate member 101' is in the straight, or substantially straight, configuration when it is disposed within the first lumen 446 of scope 440. As elongate member 101' is advanced distally, as indicated by arrow 434, and a portion, or the entirety, of elongate member curve 155' is advanced distal to the distal end 444 of scope 440, elongate member 101' begins to move from the straight, or substantially straight, configuration to the curved configuration, as illustrated in FIG. 7B. Movement of the elongate member 101' between the straight, or substantially straight, configuration to the curved configuration is considered advantageous at least because it provides a mechanism for advancing elongate member 101' distal to, or beyond, the curve 423 defined in salivary duct 422. In addition, movement of elongate member 101' between the straight, or substantially straight, configuration and the curved configuration is considered advantageous at least because it provides a mechanism for advancing elongate member 101' to a stone disposed within, or beyond, a curve 423, or that is offset from the scope 440.

In use, the distal end 104' of elongate member 101' is advanced towards stone 424 until the distal end 104' contacts stone 424. Subsequently, the firing handle of lithotripter is activated to transmit energy provided by an energy source (e.g., $CO_2$ cartridge) through elongate member 101' and to stone 424 so that it can be fragmented and removed from the salivary duct 422 using any suitable medical device, such as an irrigation device, suction device, graspers, forceps, and/or baskets.

Various methods, steps, optional steps, and alternative steps of performing lithotripsy are provided. These methods, steps, optional steps, and alternative steps include performing lithotripsy in a bodily passage, such as a salivary duct or a portion of the urinary tract. While the methods, steps, optional steps, and alternative steps of performing lithotripsy are exemplified by methods, steps, optional steps, and alternative steps of performing pneumatic lithotripsy within a salivary duct to remove a stone disposed therein, the methods, steps, optional steps, and alternative steps can include any suitable form of lithotripsy (e.g., laser lithotripsy) and can be used to treat any ailment or suitable bodily passage (e.g., urinary tract). Furthermore, while the methods, steps, optional steps, and alternative steps described herein are shown and described as a series of acts, it is to be understood and appreciated that the methods, steps, optional steps, and alternative steps are not limited by the order of acts, as some acts may, in accordance with these methods, occur in different orders, be omitted, and/or occur concurrently with other acts described herein.

Figure 8:
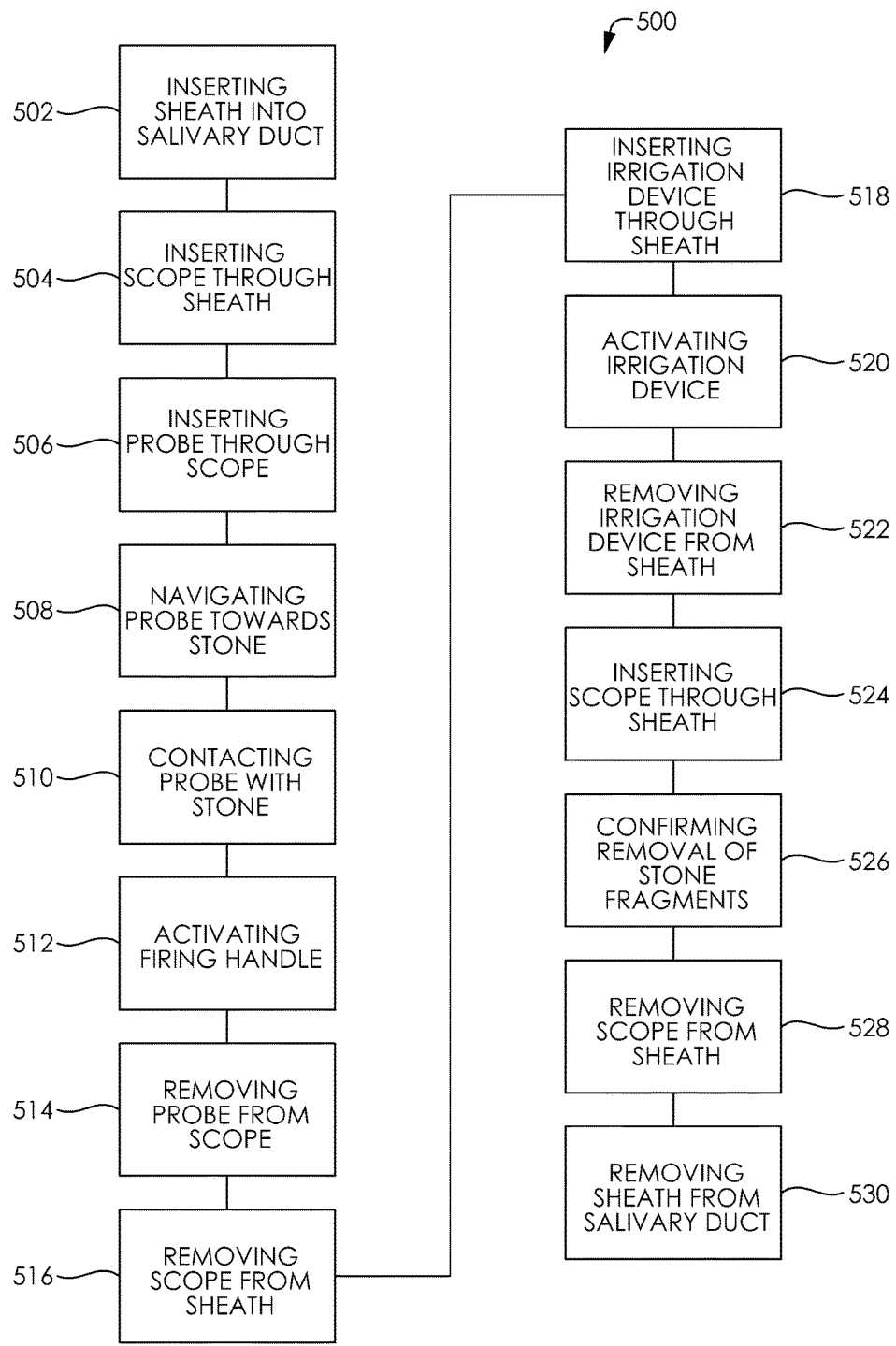
FIG. 8 is a flowchart representation of an exemplary method of treatment.

FIG. 8 is a flowchart representation of an exemplary method 500 of performing pneumatic lithotripsy using a probe to remove a stone disposed in a salivary duct having a salivary duct opening. An initial step 502 comprises inserting a sheath having a proximal end and a distal end through a salivary duct opening such that the distal end of the sheath is disposed past the salivary duct opening and in the salivary duct. The sheath defines a lumen that extends between an opening at the proximal end and an opening at the distal end of the sheath and comprises a first inner diameter and a sheath lumen length that extends from the opening at the proximal end and the opening at the distal end. Another step 504 comprises inserting a scope having a proximal end and a distal end through the lumen of the sheath such that the distal end of the scope is disposed distal to the distal end of the sheath. The scope defines at least one lumen that extends between an opening at, or near, the proximal end and an opening at the distal end of the scope, and comprises a second inner diameter and a scope lumen length that extends from the opening at, or near, the proximal end to the opening at the distal end. Another step 506 comprises inserting a lithotripter comprising a firing handle and a probe having a proximal end and a distal end through the lumen of the scope such that the distal end of the probe is disposed distal to the distal end of the scope. The probe is attached to the lithotripter and comprises an elongate member, fitting, O-ring, elongate tubular member, and a handle, and is similar to probe 300. The elongate member comprises a proximal portion, an intermediate portion, and a distal portion. The proximal portion of the elongate member has a first length and a first outer diameter. The intermediate portion of the elongate member has a second length and a second outer diameter. The distal portion of the elongate member has a third length and a third outer diameter. The first outer diameter of the proximal portion is greater than the third outer diameter of the distal portion and the third outer diameter of the distal portion is less than the second inner diameter of the lumen of the scope. The third length of the distal portion is greater than the scope lumen length. Another step 508 comprises navigating the distal end of the probe towards the stone disposed within the salivary duct. Another step 510 comprises contacting the distal end of the probe with the stone. Another step 512 comprises activating the firing handle to transmit energy through the probe and to the stone to fragment the stone. Another step 514 comprises removing the probe from the lumen of the scope. Another step 516 comprises removing the scope from the lumen of the sheath. Another step 518 comprises inserting an irrigation device having a proximal end and a distal end through the lumen of the sheath such that the distal end of the irrigation device is disposed distal to the distal end of the sheath. Another step 520 comprises activating the irrigation device to flush out the stone fragments. Another step 522 comprises removing the irrigation device from the lumen of the sheath. Another step 524 comprises inserting a scope having a proximal end and a distal end through the lumen of the sheath such that the distal end of the scope is disposed distal to the distal end of the sheath. Another step 526 comprises confirming removal of the stone fragments from the salivary duct. Another step 528 comprises removing the scope from the lumen of the sheath. Another step 530 comprises removing the sheath from the salivary duct and salivary duct opening.

The step 502 of inserting a sheath having a proximal end and a distal end through a salivary duct opening such that the distal end of the sheath is disposed past the salivary duct opening and in the salivary duct can be accomplished by locating an opening of a salivary duct and inserting the distal end of the sheath into and through the opening of the salivary duct. The opening of the salivary duct can comprise any suitable opening for completing a procedure.

Step 502 can be accomplished using any suitable sheath formed of any suitable material, having any suitable length, and defining at least one lumen, and skilled artisans will be able to select a suitable sheath based on various considerations, including the bodily passage within which a sheath is intended to be deployed. The inventor has determined that sheaths having a length between about 0.5 centimeters to about 7.0 centimeters are suitable. In addition, the inventor has determined that sheaths having a length between about 1.0 centimeter to about 5.0 centimeters are suitable. For example, the inventor has determined that sheaths having a length about, equal to, or substantially equal to, 1.0 centimeter are suitable for use in the parotid ducts or submandibular ducts. In a further example, the inventor has determined that sheaths having a length about, equal to, or substantially equal to, 5.0 centimeters are suitable for use in the submandibular ducts or submandibular ducts.

While step 502 has been described as using a sheath to provide access to a salivary duct, other devices and bodily passages are considered suitable, and skilled artisans will be able to select a suitable device and/or bodily passage according to a particular embodiment based on various considerations, such as the desired treatment intended to be performed. An example of a suitable device includes, but is not limited to, a scope defining at least one lumen. Alternatively, this step can be omitted such that a scope is inserted through a salivary duct opening such that the distal end of the scope is disposed past the salivary duct opening and in the salivary duct. Thus, method 500 can be accomplished without a sheath and using a scope.

The step 504 of inserting a scope having a proximal end and a distal end through the lumen of the sheath such that the distal end of the scope is disposed distal to the distal end of the sheath can be accomplished by locating the opening defined on the proximal end of the sheath and inserting the distal end of the scope into and through the opening of the sheath. Step 504 can be accomplished using any suitable scope formed of any suitable material, having any suitable length, and defining at least one lumen, and skilled artisans will be able to select a suitable scope based on various considerations, including the bodily passage within which a scope is intended to be deployed.

The step 506 of inserting a lithotripter comprising a firing handle and a probe having a proximal end and a distal end through the lumen of the scope such that the distal end of the probe is disposed distal to the distal end of the scope can be accomplished by locating the opening defined on, or near, the proximal end of the scope and inserting the distal end of the probe into and through the opening of the scope, as illustrated in FIG. 7.

While step 506 has been described as accomplished with a probe that comprises an elongate member, fitting, O-ring, elongate tubular member, and a handle, which is similar to probe 300, any suitable probe can be used to accomplished step 506 and method 500. Skilled artisans will be able to select a suitable probe according to a particular embodiment based on various considerations, such as the bodily passage within which a probe is intended to be used. Example probes considered suitable include, but are not limited to, probe 100, probe 101', probe 200, probe 300, any variation of the probes described herein, and any other suitable probe.

In addition, while step 506 has been described as being accomplished using a lithotripter having a firing handle, step 506 can be accomplished using any suitable lithotripter, and skilled artisans will be able to select a suitable lithotripter according to a particular embodiment based on various considerations, such as the structural configuration of a probe intended to be used with the lithotripter. Example lithotripters considered suitable to perform one or more steps, or methods, described herein include, but are not limited to, laser lithotripters, and any other lithotripter considered suitable for a particular application.

Alternative to inserting a probe through the lumen of a scope, step 504 can be omitted, and step 506 can be accomplished by inserting a probe through the lumen of a sheath.

The step 508 of navigating the distal end of the probe towards the stone disposed within the salivary duct can be accomplished by placing a distal force on any portion of the probe, handle, and/or lithotripter to provide axial movement of the distal end of the probe through the salivary duct. Step 508 can be accomplished using direct visualization, using a wire guide, and/or with the aid of a scope.

The step 510 of contacting the distal end of the probe with the stone can be accomplished using direct visualization, with the aid of a scope, and/or through tactile feedback through the probe and/or handle.

The step 512 of activating the firing handle to transmit energy through the probe and to the stone to fragment the stone can be accomplished by depressing the firing handle of the lithotripter. It is to be understood, however, that while a pneumatic lithotripter has been used as an example for performing the method 500, the methods and probe configurations described herein are not limited to pneumatic lithotripsy, and can be utilized in combination with other suitable forms of lithotripsy and to complete a procedure in any suitable bodily passage.

The step 514 of removing the probe from the lumen of the scope can be accomplished by applying a proximal force on any suitable portion of the probe, handle, and/or a portion of the lithotripter until the probe is completely removed from the salivary duct and scope.

The step 516 of removing the scope from the lumen of the sheath can be accomplished by applying a proximal force on any suitable portion of the scope until the scope is completely removed from the salivary duct and sheath. Alternatively, when a scope is passed into a salivary duct independent of a sheath, this step can comprise removing the scope from the salivary duct and the salivary duct opening. Alternatively, this step can be omitted.

The step 518 of inserting an irrigation device having a proximal end and a distal end through the lumen of the sheath such that the distal end of the irrigation device is disposed distal to the distal end of the sheath can be accomplished by locating the opening defined on the proximal end of the sheath and inserting the distal end of the irrigation device into and through the opening of the sheath. Step 518 can be accomplished using any suitable irrigation device that is adapted to introduce any suitable fluid (e.g., water, saline) into a bodily passage to assist with the removal of material (e.g., stone fragments) from the bodily passage. Alternatively, this step can be accomplished by inserting an irrigation device having a proximal end and a distal end through a lumen of the scope such that the distal end of the irrigation device is disposed distal to the distal end of the scope. Alternative to advancing an irrigation device, one or more other medical devices may be advanced through the lumen of the sheath or a lumen of the scope and used to remove the stone, and/or stone fragments, disposed within the salivary duct, and skilled artisans will be able to select a suitable medical device based on various considerations, such as the location of the stone within the salivary duct. Example medical devices considered suitable include, but are not limited to, graspers, forceps, and/or baskets.

The step 520 of activating the irrigation device to flush out the stone fragments can be accomplished by a user activating a power source to introduce any suitable fluid (e.g., water, saline) into the salivary duct to assist with the removal of material (e.g., stone fragments) from the salivary duct.

The step 522 of removing the irrigation device from the lumen of the sheath can be accomplished by applying a proximal force on any suitable portion of the irrigation device until the irrigation device is completely removed from the salivary duct and sheath. Alternatively, this step can comprise removing the irrigation device from the lumen of the scope.

The step 524 of inserting a scope having a proximal end and a distal end through the lumen of the sheath such that the distal end of the scope is disposed distal to the distal end of the sheath can be accomplished by locating the opening defined on the proximal end of the sheath and inserting the distal end of the scope into and through the opening of the sheath. Step 524 can be accomplished using any suitable scope formed of any suitable material, having any suitable length, and defining at least one lumen, and skilled artisans will be able to select a suitable scope based on various considerations, including the bodily passage within which a scope is intended to be deployed. Alternatively, this step can be omitted.

The step 526 of confirming removal of the stone fragments from the salivary duct can be accomplished using the scope, direct visualization, or any other suitable method and/or device, and skilled artisans will be able to select a suitable method and/or device to confirm removal of stone fragments from a salivary duct according to a particular embodiment based on various considerations, such as the bodily passage within which the stone fragments are disposed.

Optionally, one or more of step 506, step 508, step 510, step 512, step and 514 can be repeated if it is determined that additional stones are disposed within the salivary duct.

The step 528 of removing the scope from the lumen of the sheath can be accomplished by applying a proximal force on any suitable portion of the scope until the scope is completely removed from the salivary duct and the lumen of the sheath.

The step 530 of removing the sheath from the salivary duct and salivary duct opening can be accomplished by applying a proximal force on any suitable portion of the sheath until the sheath is completely removed from the salivary duct and the salivary duct opening. Optionally, the step of removing the scope from the lumen of the sheath can be accomplished in combination with the step of removing the sheath from the salivary duct and salivary duct opening. Optionally, this step can be omitted.

It is considered advantageous to complete method 500 in the order illustrated and/or described. In is noted however, that any order is considered suitable.

Figure 9:
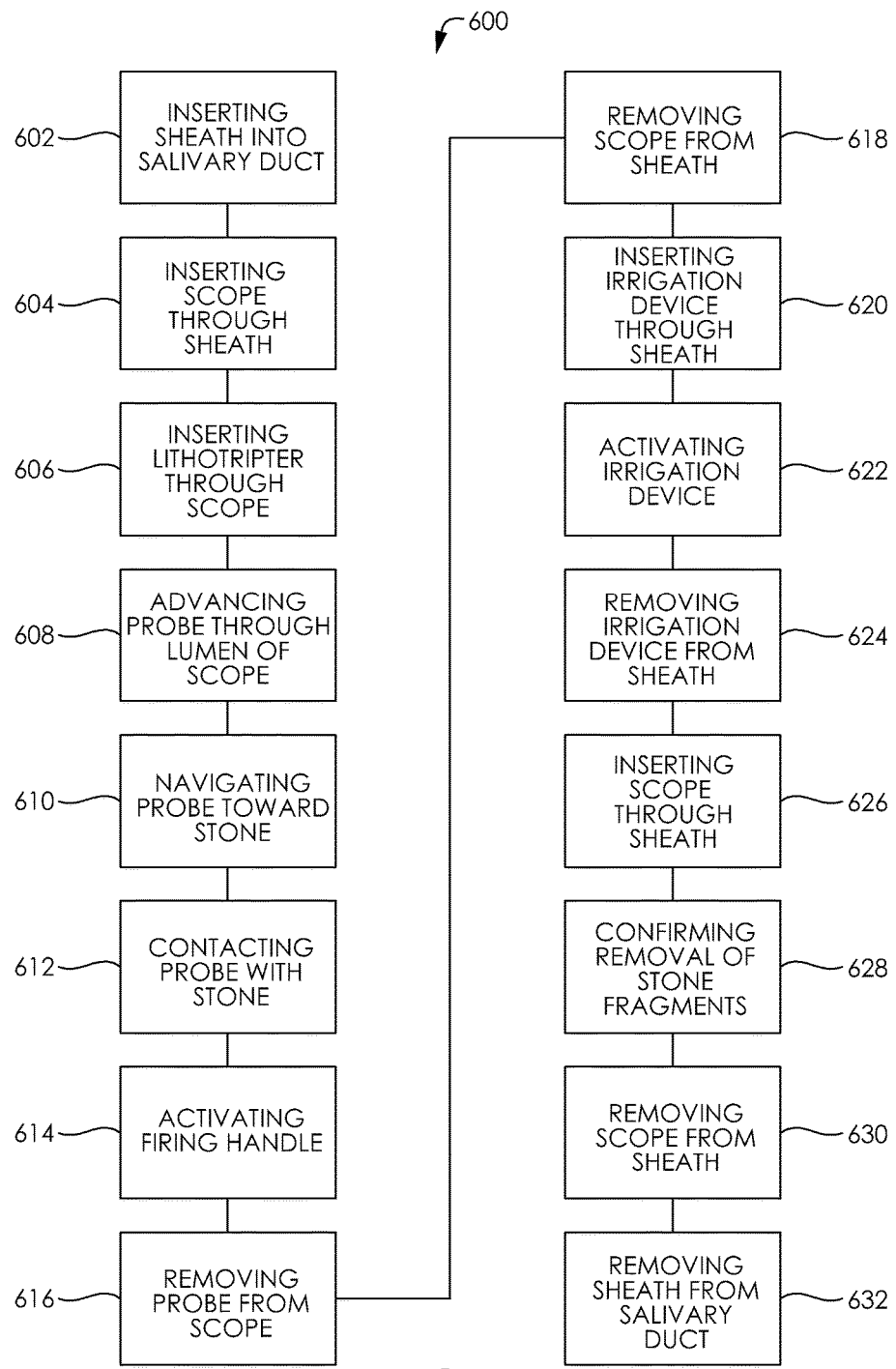
FIG. 9 is a flowchart representation of another exemplary method of treatment.

FIG. 9 is a flowchart representation of another exemplary method 600 of performing pneumatic lithotripsy using a probe to remove a stone disposed in a salivary duct. The salivary duct has a salivary duct wall defining a salivary duct opening and a curve. The stone is disposed distal to, or beyond, the curve defined by the salivary duct wall.

An initial step 602 comprises inserting a sheath having a proximal end and a distal end through the salivary duct opening such that the distal end of the sheath is disposed past the salivary duct opening and in the salivary duct. The sheath defines a lumen that extends between an opening at the proximal end of the sheath and an opening at the distal end of the sheath and comprises a first inner diameter and a sheath lumen length that extends from the opening at the proximal end and the opening at the distal end. Another step 604 comprises inserting a scope having a proximal end and a distal end through the lumen of the sheath such that the distal end of the scope is disposed distal to the distal end of the sheath. The scope defines at least one lumen that extends between an opening at, or near, the proximal end and an opening at the distal end of the scope, and comprises a second inner diameter and a scope lumen length that extends from the opening at, or near, the proximal end to the opening at the distal end. Another step 606 comprises inserting a lithotripter comprising a firing handle and a probe having a proximal end and a distal end through the lumen of the scope such that the distal end of the probe is disposed distal to the distal end of the scope. An exemplary probe considered suitable to perform method 600 is probe 101', described above. Another step 608 comprises advancing the probe through the lumen of the scope such that a portion, or the entirety, of the curve defined by the elongate member is disposed distal to the distal end of the scope. Another step 610 comprises navigating the distal end of the probe towards the stone disposed within the salivary duct. Another step 612 comprises contacting the distal end of the probe with the stone. Another step 614 comprises activating the firing handle to transmit energy through the probe and to the stone to fragment the stone. Another step 616 comprises removing the probe from the lumen of the scope. Another step 618 comprises removing the scope from the lumen of the sheath. Another step 620 comprises inserting an irrigation device having a proximal end and a distal end through the lumen of the sheath such that the distal end of the irrigation device is disposed distal to the distal end of the sheath. Another step 622 comprises activating the irrigation device to flush out the stone fragments. Another step 624 comprises removing the irrigation device from the lumen of the sheath. Another step 626 comprises inserting a scope having a proximal end and a distal end through the lumen of the sheath such that the distal end of the scope is disposed distal to the distal end of the sheath. Another step 628 comprises confirming removal of the stone fragments from the salivary duct. Another step 630 comprises removing the scope from the lumen of the sheath. Another step 632 comprises removing the sheath from the salivary duct and salivary duct opening.

While method 600 has been described as being accomplished using a sheath, it can alternatively be accomplished without a sheath and only with a scope. Thus, the steps requiring a particular component to be passed through a sheath can alternatively be passed through a lumen of a scope.

Step 602 is accomplished as described above with respect to step 502.

Step 604 is accomplished as described above with respect to step 504.

The step 606 of inserting a lithotripter comprising a firing handle and a probe having a proximal end and a distal end through the lumen of the scope such that the distal end of the probe is disposed distal to the distal end of the scope can be accomplished by locating the opening defined on, or near, the proximal end of the scope and inserting the distal end of the probe into and through the opening of the scope, as illustrated in FIG. 7A.

Alternative to inserting a probe through the lumen of a scope, step 606 can be omitted, and step 606 can be accomplished by inserting a probe through the lumen of a sheath.

Step 608 can be accomplished by placing a distal force on any suitable portion of the lithotripter and/or probe such that a portion, or the entirety, of the curve defined by elongate member 101' is advanced distal to the distal end of the scope, as illustrated in FIG. 7B. Advancing a portion, or the entirety, of curve 155' distal to, or beyond, the distal end of scope 440 is considered advantageous at least because it provides a mechanism for navigating elongate member 101' through the tortuous anatomy of a bodily passage, such as a salivary duct.

An optional step comprises rotating the lithotripter and/or probe such that the distal end of elongate member 101' is directed toward the stone disposed within the salivary duct. This step can be accomplished by applying a rotational force to the lithotripter and/or probe until the distal end of elongate member is directed toward the stone.

The remaining steps of method 600 can be accomplished as described above in method 500.

It is considered advantageous to complete method 600 in the order illustrated and/or described. In is noted however, that any order is considered suitable.

The foregoing detailed description provides exemplary embodiments of the invention and includes the best mode for practicing the invention. The description and illustration of embodiments is intended only to provide examples of the invention, and not to limit the scope of the invention, or its protection, in any manner.

What is claimed is:

1. A probe for use in lithotripsy comprising:
   an elongate member comprising a first proximal end, a first distal end, a proximal portion, an intermediate portion, and a distal portion, the proximal portion having a first length and a first outer diameter, the intermediate portion having a second length and a second outer diameter, the distal portion having a third length and a third outer diameter, the intermediate portion disposed between the proximal portion and the distal portion, the first outer diameter being greater than the third outer diameter, the second outer diameter tapering from the first outer diameter to the third outer diameter;

a fitting disposed on the first proximal end of the elongate member and adapted to attach the probe to a lithotripter, the fitting having a second proximal end and a second distal end;

an elongate tubular member disposed over a portion of the first length of the proximal portion, the elongate tubular member comprising a third proximal end disposed adjacent to the second distal end of the fitting and a third distal end disposed proximal to the first distal end of the elongate member, the entire elongate tubular member disposed between the second distal end of the fitting and the first distal end of the elongate member; and a handle disposed on the elongate member, the handle comprising a fourth proximal end attached to the third distal end of the elongate tubular member and a fourth distal end, the handle moveable between a first configuration and a second configuration, in the first configuration the elongate tubular member and the handle are slidably disposed on the elongate member, in the second configuration the elongate tubular member and the handle are releasably attached to the elongate member;

wherein the elongate tubular member has a length extending from the third proximal end to the third distal end; and wherein the handle has a length extending from the fourth proximal end to the fourth distal end, the length of the handle being less than the length of the elongate tubular member.

2. The probe of claim 1, wherein the third distal end of the elongate tubular member is disposed proximal to the intermediate portion of the elongate member; and wherein the handle is disposed over the intermediate portion of the elongate member.

3. The probe of claim 1, wherein the second length is less than the first length and the third length.

4. The probe of claim 1, wherein the first outer diameter is substantially uniform along the first length; and wherein the third outer diameter is substantially uniform along the third length.

5. The probe of claim 4, wherein the third outer diameter is about 0.56 mm.

6. The probe of claim 4, wherein the third outer diameter is about 0.40 mm.

7. The probe of claim 1, wherein the proximal portion of the elongate member is substantially rigid relative to the distal portion of the elongate member.

8. The probe of claim 1, wherein the fitting further comprises a tubular member having a first member extending radially outward from the tubular member at the second proximal end and a second member extending radially outward from the tubular member and disposed between the first member and the second distal end.

9. The probe of claim 8, wherein the fitting is attached to the elongate member.

* * * * *